(12) United States Patent
Rubbert et al.

(10) Patent No.: US 7,751,925 B2
(45) Date of Patent: Jul. 6, 2010

(54) SYSTEM TO MANUFACTURE CUSTOM ORTHODONTIC APPLIANCES, PROGRAM PRODUCT, AND RELATED METHODS

(75) Inventors: Ruedger Rubbert, Berlin (DE); Hans-Christian Krueger, Berlin (DE)

(73) Assignee: 3M Innovative Properties Company, Saint Paul, MN (US)

( * ) Notice: Subject to any disclaimer, the term of this patent is extended or adjusted under 35 U.S.C. 154(b) by 332 days.

(21) Appl. No.: 11/583,103

(22) Filed: Oct. 18, 2006

(65) Prior Publication Data
US 2007/0178423 A1 Aug. 2, 2007

Related U.S. Application Data

(60) Provisional application No. 60/763,022, filed on Jan. 27, 2006.

(51) Int. Cl.
- G06F 17/00 (2006.01)
- G06F 19/00 (2006.01)
- B21F 43/00 (2006.01)
- A61C 3/00 (2006.01)
- A61C 11/00 (2006.01)

(52) U.S. Cl. .................. 700/162; 29/896.11; 433/8; 433/22; 433/24; 433/213; 700/96

(58) Field of Classification Search .............. 29/896.11; 700/96, 162; 433/8, 22, 24, 213
See application file for complete search history.

(56) References Cited

U.S. PATENT DOCUMENTS 1,103,606 A 7/1914 Montag
1,163,196 A 12/1915 Angle
2,566,414 A 9/1951 Henry
3,738,005 A 6/1973 Cohen et al.
3,922,787 A 12/1975 Fischer et al.

(Continued)

FOREIGN PATENT DOCUMENTS

EP 0290247 11/1988

(Continued)

OTHER PUBLICATIONS

Weichmann, D.; A New Bracket System for Lingual Orthodontic Treatment, J. Orofac Orthop 2003; 64: 372-388.

(Continued)

*Primary Examiner*—Albert DeCady
*Assistant Examiner*—Thomas H Stevens
(74) *Attorney, Agent, or Firm*—Bracewell & Giuliani LLP

(57) ABSTRACT

A system to manufacture orthodontic appliances, program product, and associated methods are provided. An embodiment of a system can include a virtual orthodontic appliance design computer having orthodontic appliance design program product provided to design a virtual dimensional representation of an orthodontic appliance including bracket bodies and bracket pads, and a mold apparatus positioned to form each bracket body and bracket pad. The system also includes a data processing computer including computer-aided manufacturing program product provided to derive electrical discharge device control instructions including a virtual dimensional representation of a bracket slot in the bracket, and an electrical discharge machining apparatus. The electrical discharge machining apparatus can include a controller including control program product to derive a control signal carrying the electrical discharge device control instructions and an electrical discharge device.

43 Claims, 19 Drawing Sheets

U.S. PATENT DOCUMENTS

| | | | |
|---|---|---|---|
| 3,936,939 | A | 2/1976 | Faunce |
| 4,184,259 | A | 1/1980 | Sosnay |
| 4,219,617 | A | 8/1980 | Wallshein |
| 4,243,386 | A | 1/1981 | Kawaguchi |
| 4,284,405 | A | 8/1981 | Dellinger |
| 4,337,037 | A | 6/1982 | Kurz |
| 4,386,908 | A | 6/1983 | Kurz |
| 4,470,809 | A | 9/1984 | Klepacki |
| 4,575,337 | A | 3/1986 | Fujita |
| 4,656,860 | A | 4/1987 | Orthuber et al. |
| 5,139,419 | A | 8/1992 | Andreiko et al. |
| 5,248,257 | A | 9/1993 | Cannon |
| 5,295,886 | A | 3/1994 | Wildman |
| 5,368,478 | A | 11/1994 | Andreiko et al. |
| 5,374,187 | A | 12/1994 | Vashi |
| 5,431,562 | A | 7/1995 | Andreiko et al. |
| 5,447,432 | A | 9/1995 | Andreiko et al. |
| 5,454,717 | A | 10/1995 | Andreiko et al. |
| 5,456,600 | A | 10/1995 | Andreiko et al. |
| RE35,169 | E | 3/1996 | Lemchen et al. |
| 5,518,397 | A | 5/1996 | Andreiko et al. |
| 5,533,895 | A | 7/1996 | Andreiko et al. |
| 5,553,895 | A | 9/1996 | Karl et al. |
| 5,683,243 | A | 11/1997 | Andreiko et al. |
| 5,736,015 | A | 4/1998 | Armentrout et al. |
| 5,879,158 | A | 3/1999 | Doyle et al. |
| 5,931,667 | A | 8/1999 | Papandreas |
| 5,975,893 | A | 11/1999 | Chishti et al. |
| 6,015,289 | A | 1/2000 | Andreiko et al. |
| 6,214,285 | B1 | 4/2001 | Rubbert et al. |
| 6,217,325 | B1 | 4/2001 | Chishti et al. |
| 6,227,850 | B1 | 5/2001 | Chishti et al. |
| 6,227,851 | B1 | 5/2001 | Chishti et al. |
| 6,250,918 | B1 | 6/2001 | Sachdeva et al. |
| 6,293,791 | B1 | 9/2001 | Weinstein |
| 6,315,553 | B1 | 11/2001 | Sachdeva et al. |
| 6,318,995 | B1 | 11/2001 | Sachdeva et al. |
| 6,322,728 | B1 | 11/2001 | Brodkin et al. |
| 6,350,120 | B1 | 2/2002 | Sachdeva et al. |
| 6,382,966 | B1 | 5/2002 | Aknin |
| 6,431,870 | B1 | 8/2002 | Sachdeva et al. |
| 6,464,496 | B1 | 10/2002 | Sachdeva et al. |
| 6,471,512 | B1 | 10/2002 | Sachdeva et al. |
| 6,612,143 | B1 | 9/2003 | Butscher et al. |
| 6,632,089 | B2 | 10/2003 | Rubbert et al. |
| 6,648,640 | B2 * | 11/2003 | Rubbert et al. ................ 433/24 |
| 6,739,869 | B1 | 5/2004 | Taub et al. |
| 6,776,614 | B2 | 8/2004 | Wiechmann et al. |
| 6,846,179 | B2 | 1/2005 | Chapouland et al. |
| 6,928,733 | B2 | 8/2005 | Rubbert et al. |
| 6,988,889 | B2 | 1/2006 | Abels et al. |
| 7,155,373 | B2 | 12/2006 | Jordan et al. |
| 7,188,421 | B2 | 3/2007 | Cleary et al. |
| 7,229,282 | B2 | 6/2007 | Andreiko et al. |
| 7,240,528 | B2 | 7/2007 | Weise et al. |
| 7,335,024 | B2 * | 2/2008 | Wen .......................... 433/213 |
| 7,474,307 | B2 | 1/2009 | Chishti et al. |
| 2002/0010568 | A1 | 1/2002 | Sporbert et al. |
| 2002/0025503 | A1 | 2/2002 | Chapoulaud et al. |
| 2002/0028417 | A1 | 3/2002 | Chapoulaud et al. |
| 2004/0072120 | A1 | 4/2004 | Lauren |
| 2004/0086824 | A1 | 5/2004 | Kesling |
| 2006/0127834 | A1 * | 6/2006 | Szwajkowski et al. ......... 433/2 |

FOREIGN PATENT DOCUMENTS

| | | |
|---|---|---|
| EP | 10/80697 | 3/2001 |
| EP | 1080697 A1 | 3/2001 |
| FR | 2369828 | 11/1977 |
| WO | 9410935 A1 | 5/1994 |
| WO | WO 94/10935 | 5/1994 |
| WO | 9858596 A1 | 12/1998 |
| WO | 0111969 A1 | 2/2001 |
| WO | 0180761 A2 | 11/2001 |
| WO | WO 01/80761 | 11/2001 |

OTHER PUBLICATIONS

Mujagic, Magali, et al., Digital Design and Manufacturing of the Lingualcare Bracket System, J. Clin. Orthod Jun. 2005; 39:6:375-82.

T. Creekmore, "Lingual orthodontics—Its renaissance", American Journal of Orthodontics and Denotfacial Orthopedics, Aug. 1989; vol. 96 No. 2, pp. 120-137.

Geschaftsbereich Medizintechnik, Bending Art System, 1994, Germany.

Fillion D.; "The Thickness Measurement System with the DALI Program;" Ramano R. Lingual orthodontics, Hamilton-London: Decker; pp. 175-184 (1998).

Huge, S.A.; "The customized lingual appliance set-up service (CLASS) system;" Ramano R Lingual orthodontics, Hamilton-London: Decker; pp. 163-173 (1998).

Wiechmann, D.; "Lingual orthodontics. Part 1: Laboratory procedure;" J Orofac OrthopjFortschr Kieferorthop; vol. 60 pp. 371-379 (1999).

Wiechmann, D.; "Lingual orthodontics. Part 2: Archwire fabrication;" J Orofac OrthopjFortschr Kieferorthop; vol. 60 pp. 416-426 (1999).

Kurz, C. et al.; Lingual Orthodontics: A Status Report Part 2 Research and Development; JCO pp. 1-9 (1982).

Wiechmann, D.; "A New Bracket System for Lingual Orthodontic Treatment Part 1: Theoretical Background and Development;" J Orofac OrthopjFortschr Kieferorthop 2002; Clinical Forum; pp. 234-245 (2002).

Hiro, T.; "Resin core indirect bonding system-improvement of lingual orthodontic treatment;" J Jpn Orthod Soc; vol. 57, pp. 83-91 (1998).

Fujita, K.; "Development of lingual-bracket technique:" J Jpn Orthod Soc; vol. 37, pp. 381-384 (1978).

Geyer Medizintechnik. "Marketing brochure distributed at German Annual Orthodontic Congress 1994", Berlin, German, English version attached hereto.

Marketing brochure distributed at German Annual Orthodontic Congress 1994 by Geyer Nedizintechnick, Berlin, Germany 8 pages.

Printed Advertisement by Geyer Medizintechnik in Congress Program of German Annual Orthodontic Congress 1993; 1 page.

Creekmore, T. - Lingual Orthodontics—Ots renaissance—American Journal of Orthodontics and Dentofacial Orthopedics, 198 August; vol. 96, No. 2 pp. 120-137.

Geyer Medizintechnik, Marketing brochure distributed at German Annual Orthodontic Congress 1994, Berlin, Germany, English version attached hereto.

Kurz, C. - Lingual Orthodontics: A Status Report Part 2 Research and Development; JCO, pp. 1-9 (1982).

Partial File History of U.S. Appl. No. 11/749,860.

Partial File History of U.S. Appl. No. 11/583,103.

Partial File History of U.S. Appl. No. 10/843,897.

Partial File History of U.S. Appl. No. 10/897,149.

Partial File History of U.S. Appl. No. 11/522,674.

Partial File History of U.S. Appl. No. 11/893,632.

Stamm et al., A subjective comparison of two lingual bracket systems, European Journal of Orthodontics, 27, 2005, pp. 420-426.

Align Technology Presentation, found at (http://wvvw.aligntechinstitute.com/files/ATEArchive/pdf/ATE.Jan.2009.Invisalign%20Assist%DATE%Jan%2009.pdf, 38 pages.

P. Ling, Article tilted Clinical Limitations of lnvisaslign, Clinical Practice, found at www.cda-adc.ca/joda/vol.-73/issue-3/263.html, Apr. 2007, 4 pages.

Djeu, Outcome assessment of invisalign and traditional orthodontic treatment compared with the American Board of Orthodontics objective grading system, American Journal of Orthodontics and Dentofacial Orthopedics, Sep. 2005, 7 pages.

Hohoff, et al., Comparison of 3 bonded lingual appliances by auditive analysis and subjective assessment, American Journal of Orthod Dentofacial Orthop, 2003, 124, pp. 737-745.

English language translation of French abstract for FR 2369828, published on Jun. 2, 1978, http://babelfish.yahoo.com/translate_txt, Dec. 4, 2009.

Office Action dated Dec. 10, 2009 in co-pending U.S. Appl. No. 10/843,897.

Partial File History of U.S. Appl. No. 11/749,860, filed May 17, 2007.
Partial File History of U.S. Appl. No. 11/583,103, filed Oct. 18, 2006.
Partial File History of U.S. Appl. No. 10/843,897, filed Nov. 27, 2003.
Partial File History of U.S. Appl. No. 10/897,149, filed Jul. 22, 2004.
Partial File History of U.S. Appl. No. 11/522,674, filed Sep. 18, 2006.
Partial File History of U.S. Appl. No. 11/893,632, filed May 17 2007.

Align Technology Presentation, found at (http://wvvw.aligntechinstitute.com/files/ATEArchive/pdf/ATE.Jan.2009.Invisalign%20Assist%DATE%Jan%2009.pdf, pp. 1-38.

P. Ling, Article tilted Clinical Limitations of lnvisaslign, Clinical Practice, found at www.cda-adc.ca/joda/vol.-73/issue-3/263.html, Apr. 2007, pp. 1-4.

Djeu, Outcome assessment of invisalign and traditional orthodontic treatment compared with the American Board of Orthodontics objective grading system, American Journal of Orthodontics and Dentofacial Orthopedics, Sep. 2005, pp. 1-7.

English language translation of French abstract for FR 2369828, published on Jun. 2, 1978, http://babelfish.yahoo.com/translate_txt, Dec. 4, 2009, 1 page.

* cited by examiner

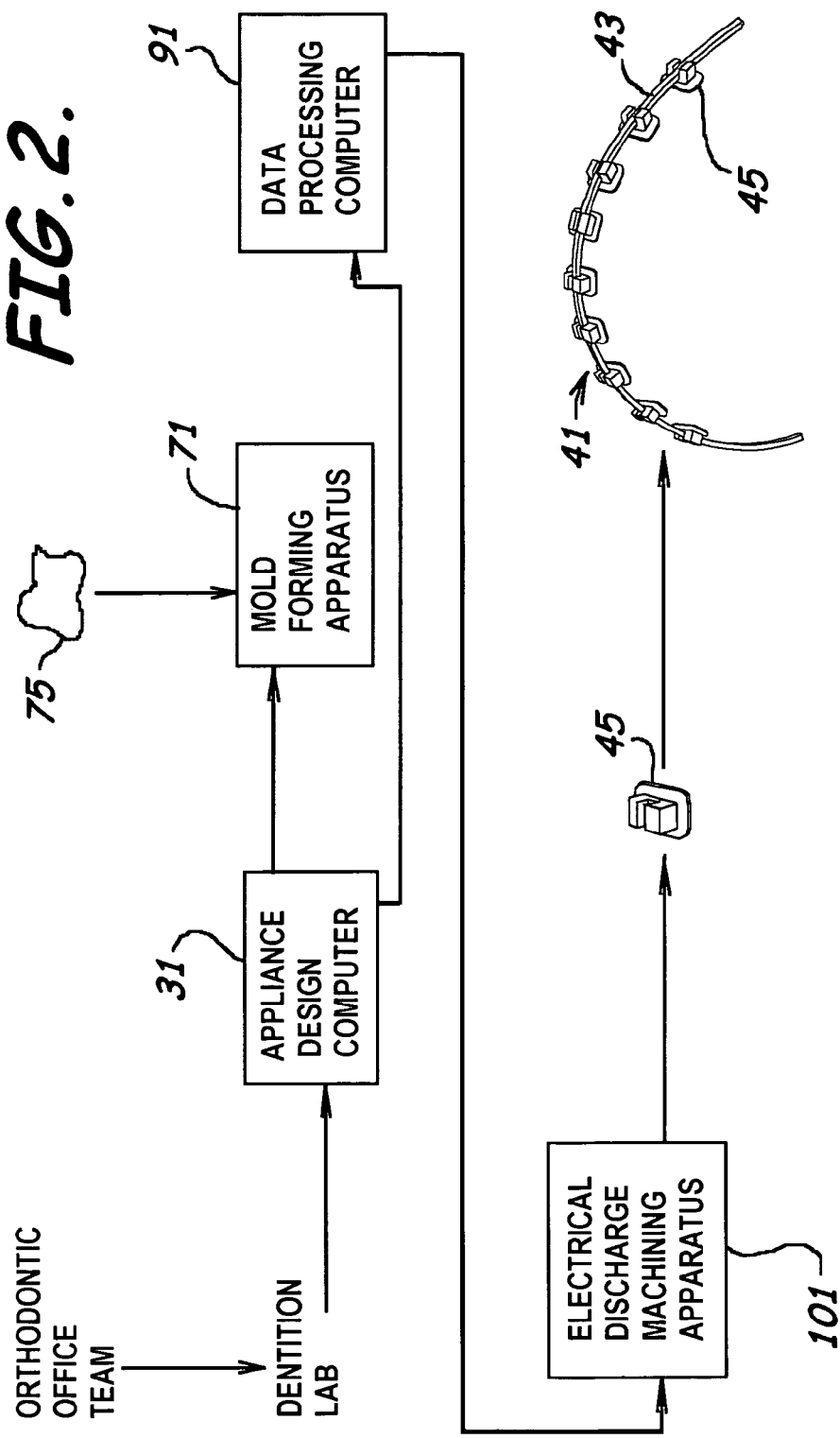

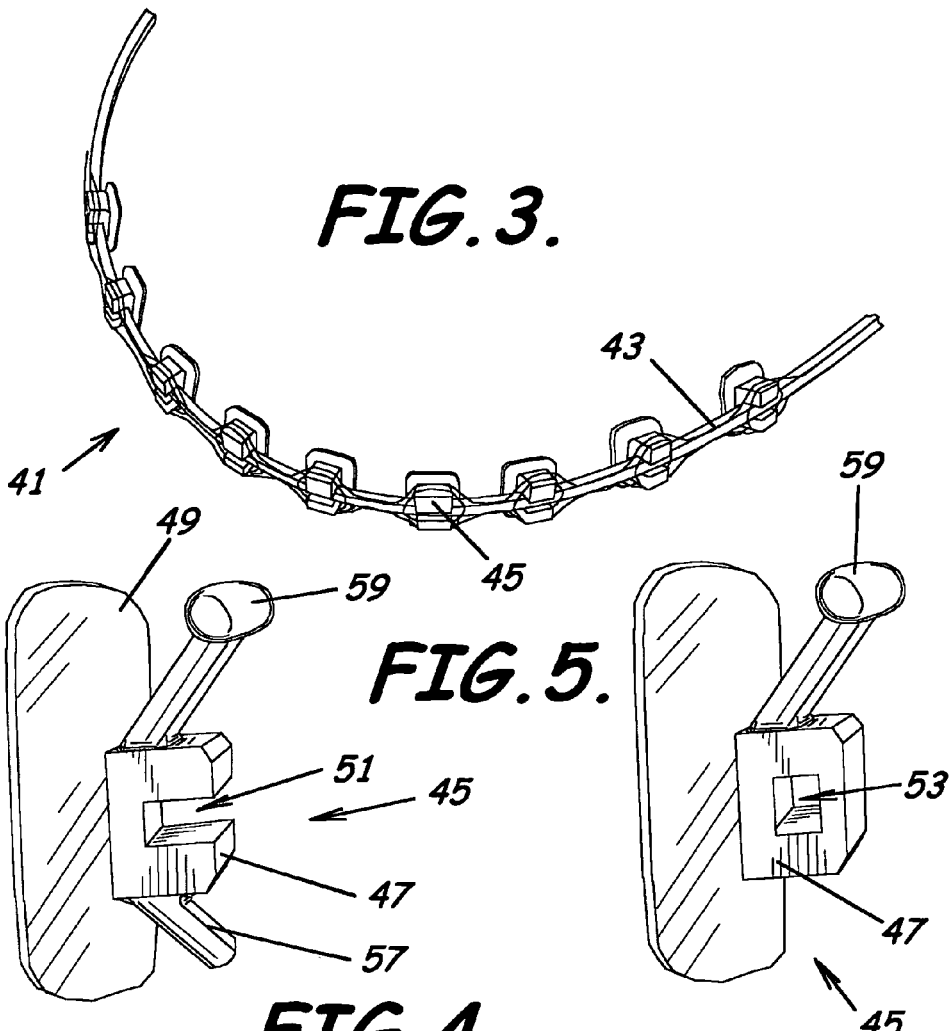
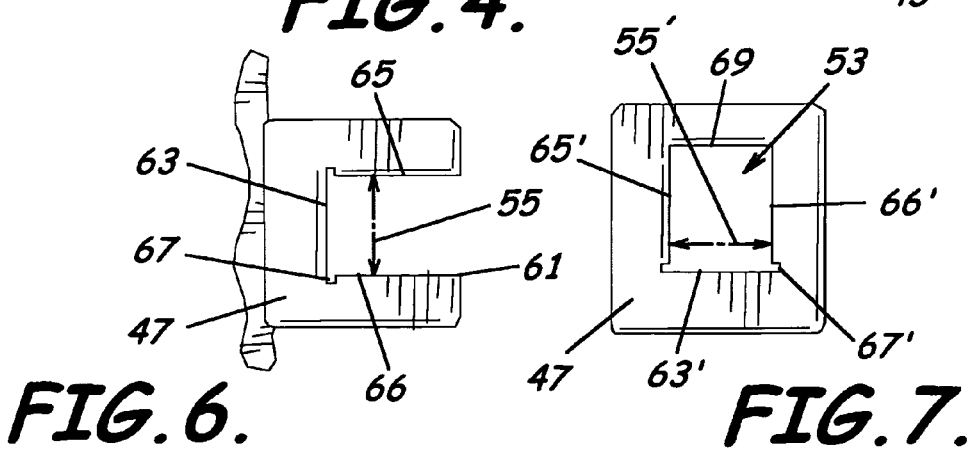

```
G91 G40 G01 X-.207 Y.39;          (FROM WAY 0,2)
G91 G42 G01 X.212 Y.212;          (CONTOUR)
G91 G42 G01 X-.504 Y.504;
G91 G42 G02 X0 Y.199 I.009 J.1;
G91 G42 G01 X.126 Y.126;
G91 G42 G02 X.199 Y0 I-.009 J.1;
G91 G42 G01 X.413 Y-.413;
G91 G42 G01 X.903 Y-.521;
G91 G40 G01 X-.142 Y-.498;        (FROM WAY 0,2)
```

FIG.23.

```
G91 G40 G01 Y-18,657;      (STARTING POINT)
M21;                       (THREAD)
G91 G42 G01 X.226 Y-.226;  (PATH FOR CONTOUR)
G91 G42 G01 X-.063 Y-.063;
G91 G42 G02 X-.19 Y0 I-.01 J.009;
G91 G42 G01 X-.252 Y.252;
G91 G42 G02 X-.002 Y.201 I.008 J.1;
G91 G42 G01 X.126 Y.126;
G91 G42 G02 X.199 Y0 I.1 J-.009;
G91 G42 G01 X.253 Y-.253;
G91 G42 G02 X0 Y-.199 I-.009 J-.1;
G91 G42 G01 X-.063 Y-.063;
G91 G40 G01 X-.226 Y.226;  (BACK TO ORIGIN)
M22;                       (DISASSEMBLE)
G91 G40 G01 Y18,657;       (BACK TO Y ABS 20)

++++++++++++++++++++++++++++++++++++++++++++++++++

REMOVE (THE BRACKETS), APPROACH FROM RIGHT

G91 G40 G01 X-.043 Y.27;   (FROM WAY 0,2)
G91 G41 G01 X0 Y.3;
G91 G41 G01 X-.326 Y.325;
G91 G40 G01 X-.3 Y0;
G91 G40 G01 X-.332 Y-.895; (TO WAY 0,2)

SYSTEM TO MANUFACTURE CUSTOM ORTHODONTIC APPLIANCES, PROGRAM PRODUCT, AND RELATED METHODS

RELATED APPLICATIONS

This application claims priority to and the benefit of U.S. Provisional Application No. 60/763,022, filed on Jan. 27, 2006, incorporated herein by reference in its entirety.

BACKGROUND OF THE INVENTION

1. Field of The Invention

The present invention relates generally to the field of orthodontics, particularly to the manufacture of orthodontic appliances. The present invention also relates to a system, program product, and related methods for designing and manufacturing orthodontic appliances for the purpose of straightening the teeth of a patient and custom precision brackets made in accordance with the methods.

2. Description of the Related Art

Orthodontic treatment applied to straighten or align teeth of a patient dates back hundreds of years. The treatment generally included use of wires wrapped around the patient's teeth. At around the mid-1970s, chiefly due to improvements in adhesive technology, the preferred method shifted to bonding brackets directly onto the teeth and running elastic wires of rectangular cross-sectional shape through slots in the bracket. Typically, the brackets are off-the-shelf products. In most cases, they are adapted to a certain tooth, for instance an upper canine, but not to the individual tooth of a specific patient. The adaptation of the bracket to the individual tooth is generally performed by filling the gap between tooth surface and bracket surface with adhesive to thereby bond the bracket to the tooth such that the bracket slot, when the teeth are moved to a finish position, lies in flat horizontal plane. The driving force for moving the teeth to the desired finish position is provided by the archwire. For lingual brackets, a system has been developed by Thomas Creekmore, for example, that has vertical bracket slots. This allows an easier insertion of the wire. The longer side of the wire is therefore oriented vertically.

The wires used in orthodontic treatment today are also generally off-the-shelf products. If they need to be individualized by the orthodontist, the goal is to do so with as few modifications as possible. According to such methodology, the brackets are designed in a manner so that at the end of treatment, when teeth are aligned, the bracket slots are supposed to be located and oriented in a planar manner. This means that a wire that would run passively through the slots, without applying any force, would be planar (flat). This treatment regimen is known as "straight wire." The further the archwire is away from the tooth surface, the more difficult it is to achieve a precise finishing position for each tooth. An error of only 10 degrees, for example, in torque (rotation around the wire axis) may well induce a vertical error in tooth position of more than 1 mm. Thus, recognized by Applicant is the need for a precision brackets slot positioned as close to the tooth surfaces as possible which, in conjunction with a customized archwire, can form a precision archwire-bracket slot interface to thereby minimize torque error.

Another problem in orthodontics is to determine the correct bracket position. At the time of bonding, teeth may be oriented far away from the desired position. So the task to locate the brackets in a manner that a flat planar archwire drives teeth to the correct position requires a lot of experience and visual imagination. The result is that at the end of treatment a lot of time is lost to perform necessary adjustments to either bracket position or wire shape. This problem can be solved by creating an ideal setup, either virtually using three-dimensional scan data of the dentition or physically by separating a dental model of the dentition into single teeth and setting up the teeth in a wax bed in an ideal position. For example, U.S. Pat. No. 6,648,640 by Rubbert et al., titled "Interactive Orthodontic Care System Based On Intra-Oral Scanning of Teeth," describes a wire-based approach to orthodontics based on generic brackets and a customized orthodontic archwire. The archwire can have complex twists and bends, and as such is not necessarily a flat planar wire. This patent document also describes a scanning system for creating three-dimensional virtual models of a dentition and an interactive, computerized treatment planning system based on the models of the scanned dentition. As part of the treatment planning, virtual brackets are placed on virtual teeth and the teeth moved to a desired position by a human operator exercising clinical judgment. The three-dimensional virtual model of the dentition plus brackets in a malocclused condition is exported to a rapid prototyping device for manufacture of a physical model of the dentition plus brackets.

U.S. Pat. No. 6,776,614 by Wiechmann et al., titled "Modular System for Customized Orthodontic Appliances," describes a wire-based approach to orthodontics based on customized orthodontic brackets and a customized orthodontic archwire. This patent document further describes designing the brackets on a computer as a combination of three-dimensional virtual objects including a virtual bracket bonding pad and a virtual bracket body retrieved from a library of virtual bracket bodies. The virtual brackets can be represented as a file containing digital shape data and can be exported to a rapid prototype fabrication device.

Recent developments in orthodontics include the use of rapid prototyping technology to form the brackets. Rapid prototyping machines can be used for models of the brackets which are then used to form molds to form the brackets. These molds generally have a cavity defining the bracket and can have a channel forming a pathway to pour bracket-forming material into the mold. Solidified bracket-forming material remaining in the channel forms a runner which must be removed. Also, if the bracket slot is not formed as part of the molding process, a bracket slot must be cut into the bracket body.

Various methodologies of forming the bracket slot can include casting, grinding or milling. For example, WO94/10935 by Andreiko et al. titled "Custom Orthodontic Appliance Forming Method and Apparatus" describes forming brackets by cutting custom slots in bracket blanks while preserving the base inclination angle, or alternatively, inclining the bracket bases or pads; and forming bracket bases either contoured to conform to the surfaces of the teeth or interfaced with a bonding agent to fill the space between the bracket base and the tooth. Andreiko et al., although primarily describing forming the brackets using a mechanical cutter blade, also introduces without further elaboration that other means such as wire electrical discharge machining, machining, casting, or stereo lithography, may be employed.

Such methodologies are deficient in describing systems, apparatus, or methods for creating a highly-precise bracket slot, creating an undercut in the sidewalls of the bracket slots, cutting an investment cast bracket off a runner, or cutting a highly precise tube into the bracket body. Although the desire for precision brackets has been noted in Weichmann, D, "A New Bracket System for Lingual Orthodontic Treatment, Part 2: First Clinical Experiences and Further Development," J. Orofac Orthop (2003), there has not been recognition, until now by the Applicant, of the need for a system, apparatus, program product, and methods of forming enhanced precision bracket slots or tubes using electrical discharge machining technology having such desirable features.

SUMMARY OF THE INVENTION

In view of the foregoing, embodiments of the present invention beneficially provide a system, program product, and method of manufacturing orthodontic appliances which can provide enhanced precision in forming a precision customized bracket slot in each bracket body of the orthodontic appliance. For example, according to embodiments of the present invention, bracket slot configurations can be formed that were not previously able to be formed. Further, according to embodiments of the present invention, a custom archwire and each of the precision custom bracket slots can form a high-precision archwire-bracket slot interface which can significantly reduce or minimize torque error. Recognized by the Applicant is that use of electrical discharge machining in conjunction with virtual bracket design, if employed to form the bracket slot in the bracket body, can provide enhanced precision and can allow for runner removal. Still further, according to an embodiment of the present invention, electrical discharge machining in conjunction with virtual bracket design can provide enhanced precision and can allow for manufacturing process runner removal.

More specifically, in an embodiment of the present invention, a system to manufacture orthodontic appliances can include a virtual orthodontic appliance design computer having a processor, memory coupled to the processor, and orthodontic appliance design program product stored in the memory. The orthodontic appliance design program product can include instructions to perform the operation of receiving patient dentition data typically obtained through various methodologies known to those skilled in the art and can include those to perform the operation of designing a virtual dimensional representation of the orthodontic appliance defining virtual orthodontic appliance design data in response to the received patient dentition data. The orthodontic appliance can include an archwire which, for example, can be customized, and a plurality of precision customized brackets each including a bracket body having a tooth facing bonding surface, a bracket pad connected to the bracket body, and a bracket slot.

The system can also include a mold forming apparatus which can utilize various techniques, such as, for example, rapid prototyping to create a mold used to thereby form the custom brackets. According to an embodiment of the present invention, the mold can be configured to simultaneously form both the bracket body and bracket pad and is positioned to receive a bracket-forming material. The mold forming apparatus also includes a device positioned to dispense the bracket-forming material into the mold. Each mold generally has a cavity for each of the brackets and for defining peripheries of the bracket when the bracket-forming material is positioned therein, and a channel for defining peripheries of a runner when filled with the bracket-forming material. Each molded bracket body can be connected to the runner when removed from the mold.

The system can also include a data processing computer positioned, for example, in communication with the virtual orthodontic appliance design computer through a computer network and having memory and computer-aided manufacturing program product stored in the memory. The computer-aided manufacturing program product can include instructions to perform the operation of deriving electrical discharge device control instructions readable by a machine to perform the operation of forming the bracket slot responsive to the virtual orthodontic appliance design data.

The system also includes an electrical discharge machining apparatus in communication with the data processing computer, for example, through the computer network or other communication medium known to those skilled in the art. The electrical discharge machining apparatus can include a controller having memory which can provide for computer numerical control. The controller can also include data communication program product stored in the memory which can include instructions to perform the operation of receiving or importing the electrical discharge device control instructions. The controller can also include control program product which can include instructions to derive a control signal carrying the electrical discharge device control instructions responsive to the received electrical discharge device control instructions.

The electrical discharge machining apparatus can also include an electrical discharge device having an electrical discharge electrode assembly including an electrode. The electrodes of the electrical discharge device, for example, can come in two forms, a traveling wire electrical discharge electrode or traveling wire electrode and a die-sinker electrical discharge electrode. The electrical discharge device can include at least one drive section adapted to position the bracket in electrical discharge contact with the electrode to form the bracket slot and to simultaneously separate the bracket from the runner when forming the bracket slot responsive to the control signal, depending upon the type of bracket slot being formed.

According to an embodiment of the present invention a system to fabricate or manufacture orthodontic appliances can include a numerical control data processor defining a controller having memory and control program product stored in the memory. The control program product can include instructions to perform the operation of deriving a numerical control signal carrying electrical discharge device control instructions to form a bracket slot in a bracket body of a bracket of an orthodontic appliance and to separate the bracket body from a runner connected to the bracket body. The system can also include an electrical discharge device in communication with the controller. The electrical discharge device can have an electrical discharge electrode assembly including an electrode and at least one drive section adapted to position the bracket body of the bracket in electrical discharge contact with the electrode responsive to the numerical control signal to form the bracket slot and to simultaneously separate the bracket body from the runner when forming the bracket slot.

According to an embodiment of the present invention, a system to fabricate or manufacture orthodontic appliances can include a controller having memory, data communication program product stored in the memory including instructions to perform the operation of receiving electrical discharge device control instructions describing a virtual dimensional representation of a bracket slot in a bracket body of a bracket of an orthodontic appliance, and control program product also stored in the memory including instructions to perform the operation of deriving a control signal carrying the electrical discharge device control instructions responsive to the electrical discharge device control instructions. The system can also include an electrical discharge device in communication with the controller having an electrical discharge electrode assembly including an electrode and having at least one drive section adapted to position the bracket body of a bracket in electrical discharge contact with the electrode, responsive to the control signal, to form the bracket slot according to a predefined electrical discharge cutting pattern, for example, derived to substantially match associated dimensions of a preselected archwire. Beneficially, for example, this allows for the formation of an enhanced precision interface with the archwire.

Further, embodiments of the present invention also include methods of manufacturing orthodontic appliances. For example, according to an embodiment of the present invention, a method of manufacturing orthodontic appliances includes performing the step of deriving a control signal carrying device control instructions from a virtual dimensional representation of a bracket slot in a bracket body of a bracket of an orthodontic appliance. The device control instructions, for example, describe operations to execute an electrical discharge cutting pattern extending along a perimeter of the bracket slot and customized to substantially match associated dimensions of a preselected archwire to thereby form a precision interface with the archwire. The method can also include a step of executing the electrical discharge cutting pattern responsive to the control signal to form the bracket slot. If the bracket body is connected to a runner, for example, the method can also include the step of executing the electrical discharge cutting pattern including cutting the bracket body from the runner to separate the bracket body from the runner when forming the bracket slot. Where the bracket slot is an open-ended bracket slot, the slot can be formed adjacent the runner such that the bracket can be substantially simultaneously separated from the runner upon completing the forming of the bracket slot. According to an embodiment of the present invention, a transverse extension defining an undercut in the bracket slot also can be formed in the bracket body adjacent the closed-end of the bracket slot. Further, advantageously, where the bracket slot is a tube, the slot can be first cut using a first cutting pattern, and an associated runner, if attached, can be separated from the bracket body according to a second cutting pattern.

According to an embodiment of the present invention, a method of manufacturing an orthodontic appliance can include the step of deriving a control signal carrying device control instructions from a virtual dimensional representation of a bracket slot in a bracket body of a bracket of an orthodontic appliance describing operations to execute an electrical discharge cutting pattern extending along a perimeter of the bracket slot and customized to substantially match associated dimensions of a preselected archwire. Beneficially, the result includes the formation of an enhanced precision interface with the archwire and a bracket slot having a closed perimeter to thereby define a bracket tube. The method can also include the step of executing the electrical discharge cutting pattern, responsive to a control signal, to form the bracket tube.

According to another embodiment of the present invention, a method of manufacturing an orthodontic appliance can include the step of deriving a control signal carrying device control instructions from a virtual dimensional representation of a bracket slot in a bracket body of a bracket of an orthodontic appliance describing operations to execute an electrical discharge cutting pattern to form the bracket slot. The bracket slot, according to this embodiment, has an open surface end and a closed base end and two spaced-apart sides extending therebetween. The method can also include the step of executing the electrical discharge cutting pattern responsive to a control signal. The electrical discharge cutting pattern can extend along a perimeter of the bracket slot and can form a transverse extension extending into the bracket body from one of the spaced-apart sides at the base end of the bracket slot to thereby define a bracket slot undercut.

A method of manufacturing an orthodontic appliance can include the steps of deriving a control signal carrying device control instructions describing operations to execute an electrical discharge cutting pattern to separate a bracket body of a bracket of an orthodontic appliance from a runner connected thereto, and executing the electrical discharge cutting pattern responsive to a control signal.

Beneficially, embodiments of the present invention provide a manufacturing system and methods for manufacturing a highly-precise bracket slot, creating an undercut in the sidewalls of the bracket slots, cutting an investment cast bracket off a runner, and cutting a highly precise tube into the bracket body. Embodiments of the present invention provide a manufacturing system for fabricating at least one design feature of an orthodontic appliance or a part thereof including a data processing system deriving a control signal carrying machine control instructions from a virtual dimensional representation of the design feature and a manufacturing system fabricating the design feature that includes electrical discharge machining, which can provide a level of precision and efficiency not otherwise available in systems not employing electrical discharge sheeting. Embodiments of the present invention relate to a manufacturing system and methods for manufacturing features of an orthodontic appliance or parts thereof utilizing electrical discharge machining, which in an implementation of an embodiment provide for cutting a slot of a bracket with wire-cut EDM technology such as, for example, the Mitsubishi wire EDM SX 10.

BRIEF DESCRIPTION OF THE DRAWINGS

So that the manner in which the features and benefits of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope since it may include other effective embodiments as well.

FIG. 2 is a schematic diagram of a process flow to manufacture orthodontic appliances according to an embodiment of the present invention;

FIG. 3 is a perspective view of an orthodontic appliance according to an embodiment of the present invention;

FIG. 4 is a perspective view of a bracket of an orthodontic appliance according to an embodiment of the present invention;

FIG. 5 is a perspective view of a bracket of an orthodontic appliance according to an embodiment of the present invention;

FIG. 6 is a perspective view of a bracket slot of a bracket of an orthodontic appliance according to an embodiment of the present invention;

FIG. 7 is a perspective view of a bracket slot of a bracket of an orthodontic appliance according to an embodiment of the present invention;

FIG. 23 is a sequence of numerical code in ASCII format provided to execute to an electrical discharge cutting pattern illustrated in FIG. 22 according to an embodiment of the present invention;

FIG. 27 is a sequence of numerical code in ASCII format provided to execute to an electrical discharge cutting pattern illustrated in FIG. 26 according to an embodiment of the present invention.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

As illustrated in FIGS. 1-27, embodiments of the present invention advantageously provide a new system, program product, and methods for fabricating features of an orthodontic appliance or parts thereof utilizing electrical discharge machining, and in an implementation of an embodiment, "cutting" or shaping various features of the appliance using traveling wire electrical discharge machining technology. The meaning of "CAD" shall include but shall not be limited to any and all technology of computer aided design. The meaning of "CAM" shall include but shall not be limited to any and all technology of computer aided manufacturing. The meaning of "CNC" or "machine control" shall include but shall not be limited to any and all technology of computer numerical control as it relates to manufacturing machinery and systems, including but not limited to rapid prototyping devices and systems. The meaning of "cut" shall include performing electrical erosion. The meaning of "EDM" or "EDM-ing" shall include but shall not be limited to any and all technology of electrical discharge machining. The term "3D" shall mean three-dimensional. The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim should be understood as being generic to all possible meanings supported by the specification and by the word itself.

Figure 1:
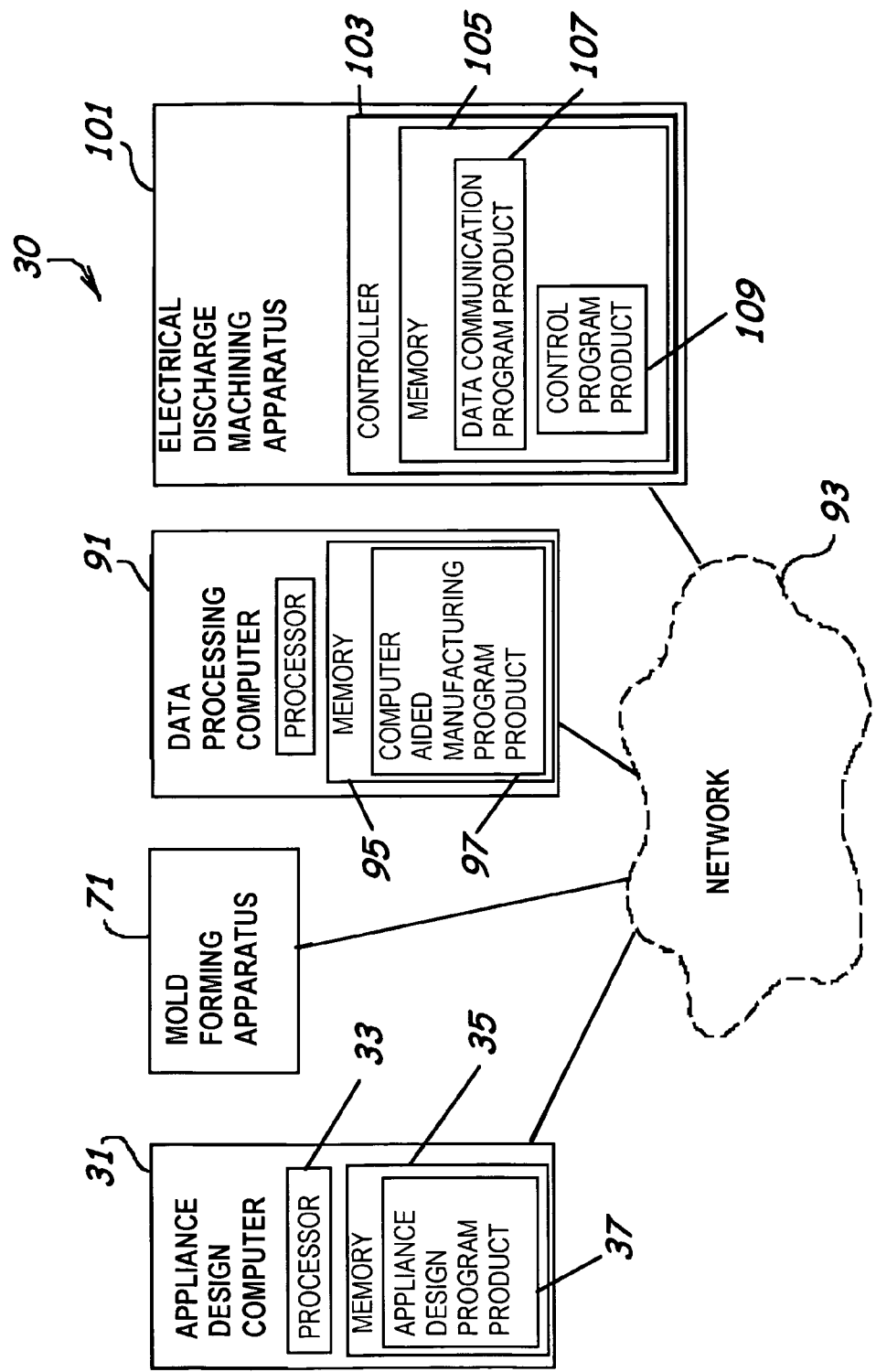
FIG. 1 is a schematic block diagram of a system to manufacture orthodontic appliances according to an embodiment of the present invention.

As shown in FIGS. 1 and 2, an embodiment of a system 30 to fabricate or manufacture orthodontic appliances can include a virtual orthodontic appliance design computer 31 having a processor 33, memory 35 coupled to the processor 33, and orthodontic appliance design program product 37 stored in the memory 35. The orthodontic appliance design program product 37 can include instructions to perform the operation of receiving patient dentition data typically obtained through various methodologies known to those skilled in the art and can include those to perform the operation of designing a virtual dimensional representation of the orthodontic appliance 41 defining virtual orthodontic appliance design data in response to the received patient dentition data.

As shown in FIGS. 4-7, the orthodontic appliance 41 can include a customized archwire 43 and multiple of precision customized brackets 45 each including a bracket body 47, a bracket pad 49 connected to the bracket body 47, and a bracket slot 51, 53, in the bracket body 47 having a bracket slot width 55. The bracket body 47 can also include a bracket wing 57, bracket hook 59, or other design feature known to those skilled in the art. The open-end bracket slot 51 can include an open surface end 61, a closed base end 63, and two sides 65, 66, extending therebetween. The open-end brackets slot 51 (see FIGS. 4 and 6) can also include a transverse extension or extensions adjacent the base end 63 and extending into the bracket body 47 from one or both of the sides 65, 66, forming an undercut 67 having a width exceeding that of the slot width 55. The portion of the bracket body 47 adjacent the open surface end 61 can be arcuate or can have a more planar shape. The sides 65, 66, and base 63 of the bracket slot 51 can have a substantially planer surface, and, correspondingly, can be specified as having a dimensional tolerance of less than 30 microns and preferably as low as approximately eight microns, for example, along the slot width 55. The closed end (tube) bracket slot 53 (see FIGS. 5 and 7) can include a closed surface end 69 but is otherwise similar to the open-end bracket slot 51. That is, the closed-end bracket slot 53 also includes a base 63', a pair of sides 65', 66', a width 55' and can include an undercut 67'. Also similarly, the bracket tube slot 53 can be specified as having a tolerance of less than 30 microns and preferably as low as approximately eight microns along its respective slot width 55'.

Figure 8:
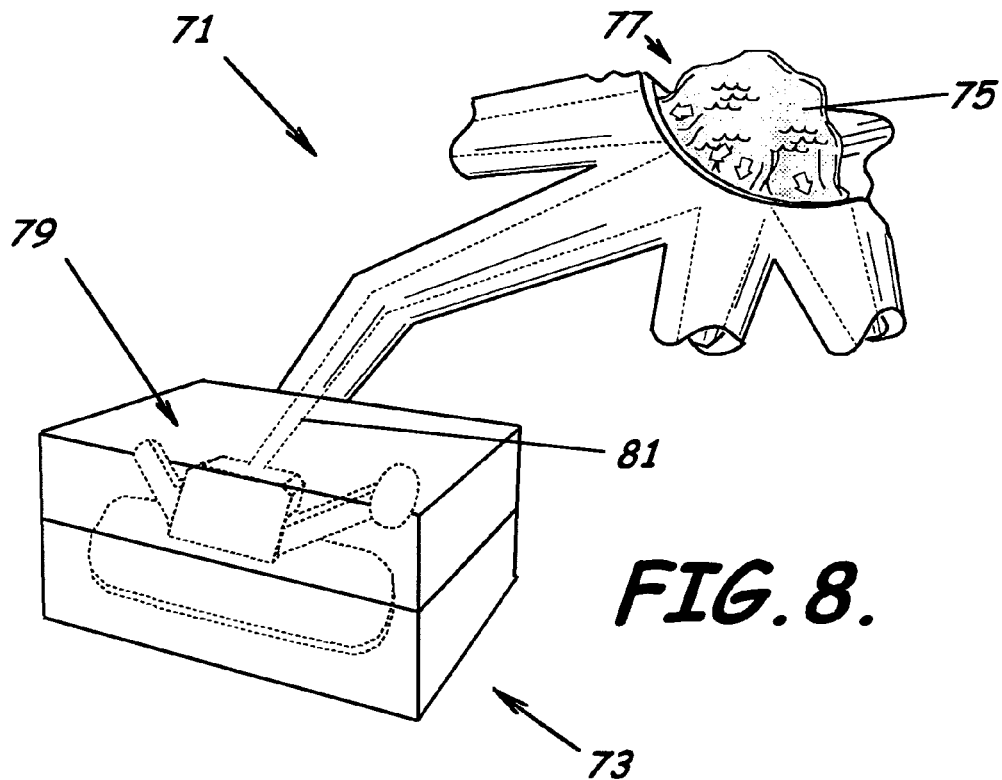
FIG. 8 is a perspective view of a mold-forming apparatus according to an embodiment of the present invention.
Figure 9:
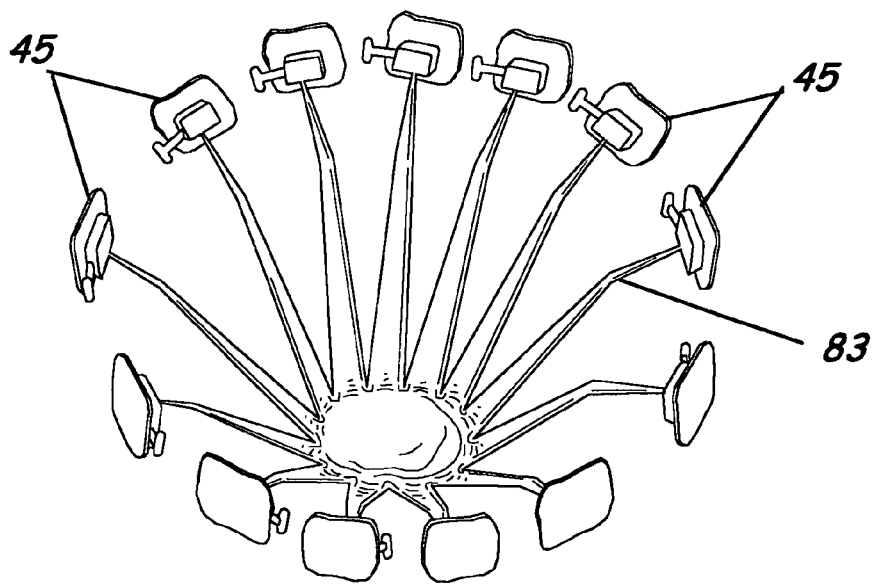
FIG. 9 is a perspective view of a mold tree according to an embodiment of the present invention.

As shown in FIG. 8, the system 30 can also include a mold forming apparatus 71, as known to those skilled in the art, which can utilize various techniques, such as, for example, rapid prototyping to form a mold 73 used to thereby form the custom brackets 45. The various rapid prototyping techniques, for example, can include stereo lithography, laminated object manufacturing, selective laser sintering, fused deposition modeling, solid ground curing, and 3-D inkjet printing, just to name a few. According to an embodiment of the present invention, the mold 73 is configured to simultaneously form both the bracket body 47 and bracket pad 49. The mold 73 is positioned to receive a bracket-forming material 75 and a dispensing device 77 positioned to dispense the bracket-forming material 75 into the mold 73. In an embodiment of the present invention, as perhaps best described in U.S. Pat. No. 6,776,614 by Wiechmann et al. titled "Modular System for Customized Orthodontic Appliances," incorporated herein by reference in its entirety, a rapid prototyping technique is used whereby a computer aided design of the bracket 45, both body 47 and pad 49, formed from a three-dimensional scan of impression of the teeth of a patient, is used to fabricate, e.g., wax or resin, models of the bracket 45 which are then used to form, e.g., cement, molds 73 of the brackets 45. Each mold 73 generally has a cavity 79 for each of the of brackets 45 and for defining peripheries of the bracket body 47 and bracket pad 49 when the bracket-forming material 75 is positioned therein and a channel 81, defining peripheries of a runner 83 (FIG. 9) when filled with the bracket material 75. As perhaps best shown in FIG. 14, each molded bracket body 47 can be connected to the runner 83 when removed from the mold 73.

As shown in FIGS. 1 and 2, the system 30 can also include a data processing computer 91 positioned, for example, in communication with the virtual orthodontic appliance design computer 31 through a computer network 93 and having memory 95 and computer-aided manufacturing program product 97 stored in the memory 95. The computer-aided manufacturing program product 97 can include instructions to perform the operation of deriving electrical discharge device control instructions readable by a machine to perform the operation of forming the bracket slot 51, 53, in response to the virtual orthodontic appliance design data. That is, the electrical discharge device control instructions can include those to perform the operation of executing an electrical discharge cutting pattern extending along a perimeter of the bracket slot 51, 53. The instructions can also include those to perform the operation of simultaneously separating the bracket body 47 from a fixture portion of the runner 83 when forming the bracket slot 51, 53. Note, according to an embodiment of the present invention, the virtual orthodontic appliance design data can be manually inputted to, or otherwise received by, the data processing computer 91. Such methodology can be used when a design feature, e.g., bracket slot width 55, 55', is described by a limited number of parameters. If the design feature represents a more complex feature, then providing design input from a virtual orthodontic appliance design computer 31 would be preferable. Note, the memory 95 along with other described memory can include volatile and nonvolatile memory known to those skilled in the art including, for example, RAM, ROM, and magnetic or optical disks, just to name a few. Note also, the computer-aided manufacturing program product electrical discharge device control instructions can be in the form of microcode, programs, routines, and symbolic languages that provide a specific set or sets of ordered operations that control the functioning of the hardware and direct its operation, as known and understood by those skilled in the art. According to an embodiment of the present invention, the instructions are geared specifically for use by a numerical control device as known and understood by those skilled in the art.

As shown in FIGS. 1 and 2, the system 30 also includes an electrical discharge machining apparatus 101 in communication with the data processing computer 91 through, for example, the computer network 93, using, e.g., an RS-232-C serial communication port, or other communication medium known to those skilled in the art. The electrical discharge machining apparatus 101 can include a controller 103, e.g., machine control unit, having memory 105, which can provide for computer numerical control. The controller 103 can also include a user input device or devices known to those skilled in the art and data communication program product 107 stored in the memory 105 which can include instructions to perform the operation of receiving or importing the electrical discharge device control instructions. The controller 103 can also include control program product 109, which includes instructions to derive a control signal carrying the electrical discharge device control instructions in response to the received electrical discharge device control instructions. Note, according to an embodiment of the present invention communication between, the controller 103 can alternatively receive (import) the electrical discharge device control instructions from the data processing computer 91 through manual data transfer using, for example, a portable computer readable medium.

Figure 10:
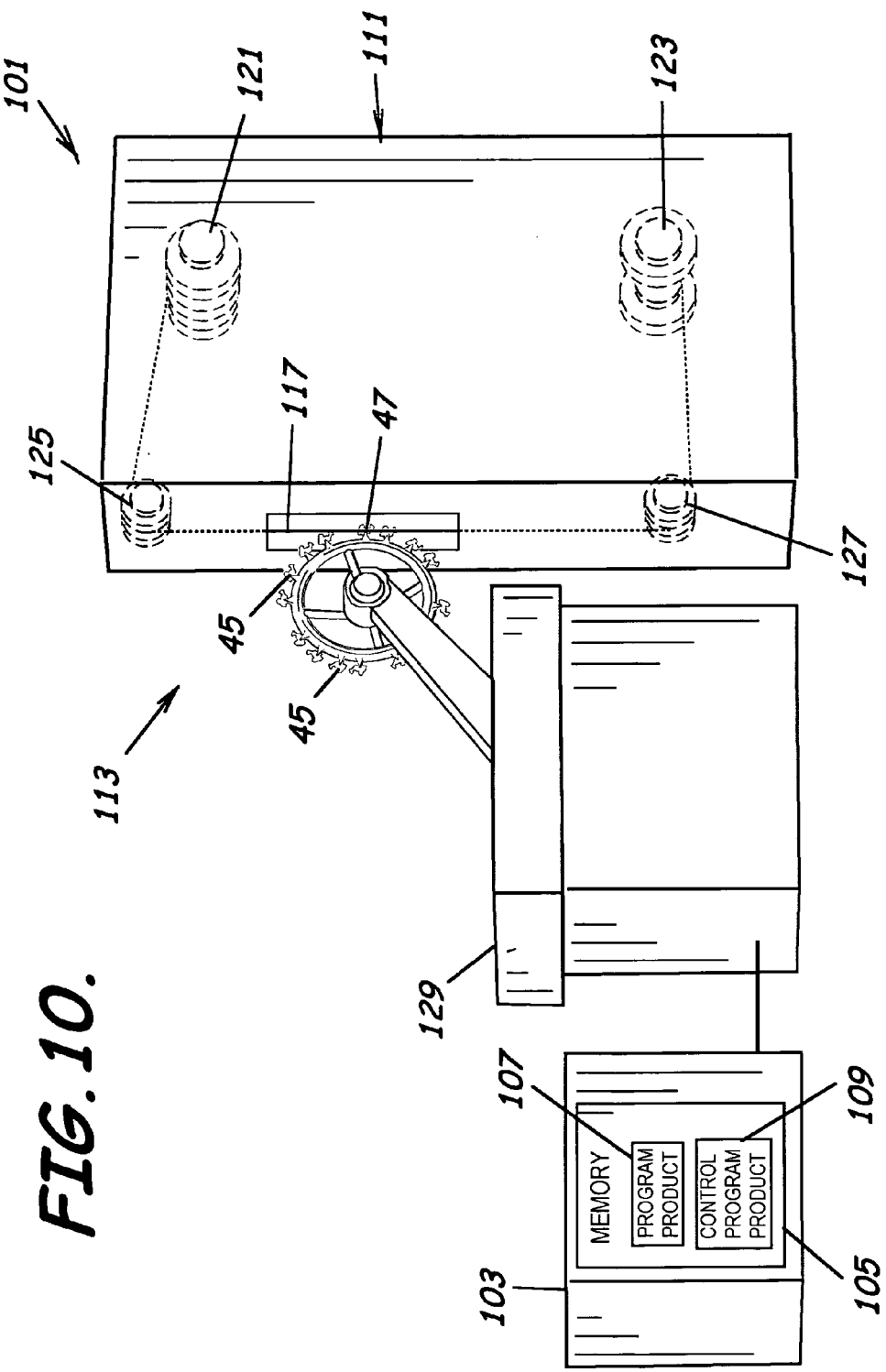
FIG. 10 is a perspective view of an electrical discharge apparatus according to an embodiment of the present invention.
Figure 11:
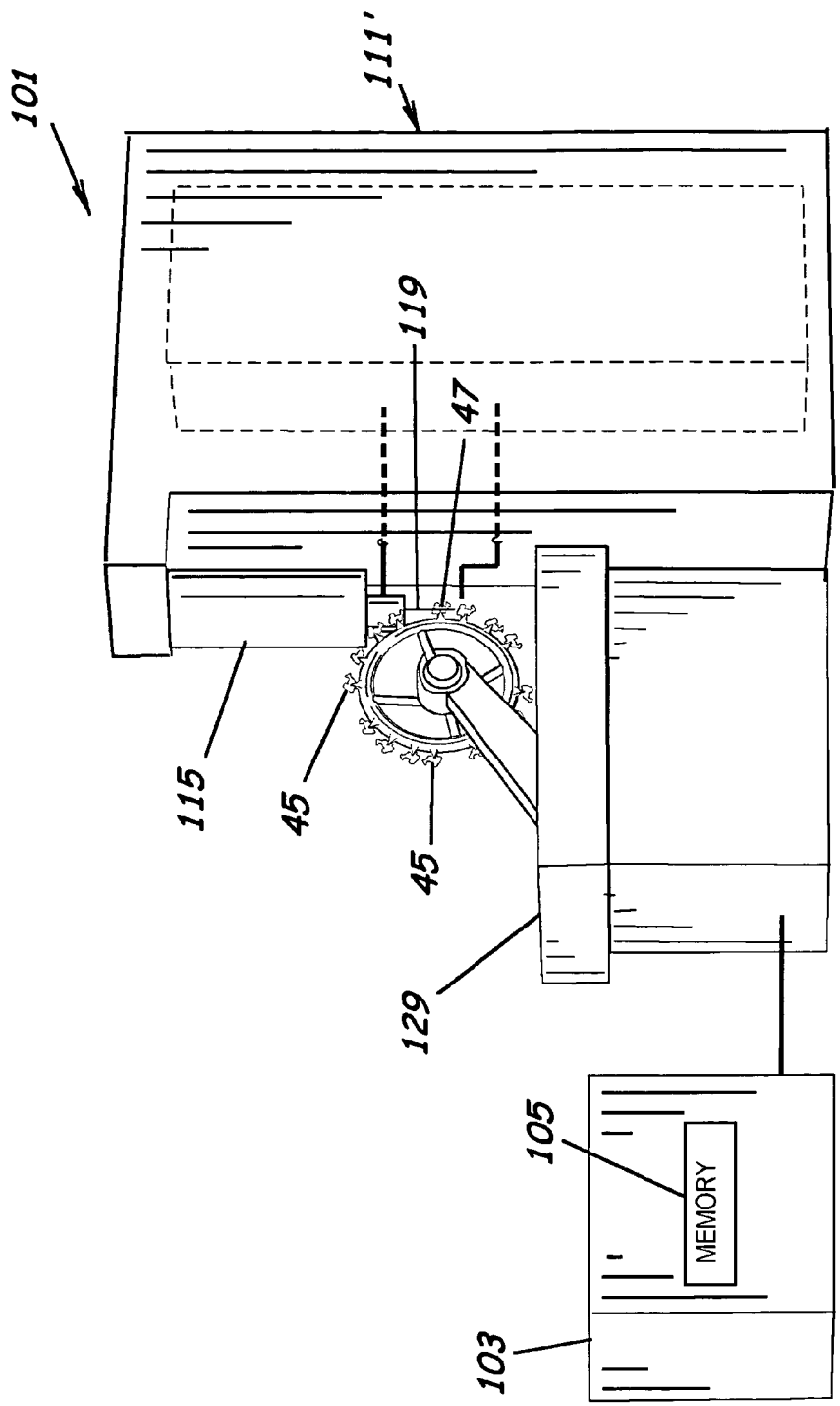
FIG. 11 is a perspective view of an electrical discharge apparatus according to an embodiment of the present invention.

As shown in FIGS. 10 and 11, the electrical discharge machining apparatus 101 can also include an electrical discharge device 111, 111', having an electrical discharge electrode assembly 113, 115, including an electrode 117, 119. A typically DC power supply and a spark controller in electrical communication with the DC power supply (not shown) provides a high frequency pulse wave which forms a corresponding high frequency series of electrical spark discharge arcs between the electrode 117, 119, and the portion of the bracket body 47 adjacent the electrode 117, 119. The electrodes of the electrical discharge device 111, 111', for example, can come in two forms, a traveling wire electrical discharge electrode or traveling wire electrode 117 (FIG. 10) and a die-sinker-electrical discharge electrode 119 (FIG. 11).

As shown in FIG. 10, the electrode assembly 113 of an electrical discharge device 111 utilizing a traveling wire electrode 117 includes a supply reel or spool 121 containing unused portions of the traveling wire electrode 117 to provide a continuous stream of supply traveling wire electrode when executing the cutting pattern and a take-up reel or spool 123 containing used portions of the traveling wire electrode to collect the traveling wire electrode supplied from the supply reel 121 when executing the cutting pattern to form the bracket slot 51 and to provide tension to the traveling wire electrode 117. Positioned between the supply reel 121 and the take-up reel 123 are a supply wire guide 125 and a take-up-wire guide 127. The wire electrode 117, constantly fed from the supply reel 123 during cutting operations, is held between the supply and take-up guides 125, 127. The traveling wire electrode 117 typically uses water as its dielectric which can be dispensed through nozzles (not shown) positioned adjacent the bracket body 47. Electrode negative polarity can be selected to enhance manufacturing speed. Electrode positive polarity can be selected to produce a more refined bracket slot surface. A combination of the two also can be used, as desired or as necessary.

According to an embodiment of the present invention, the electrical discharge device 111 includes an electrical discharge apparatus drive table 129, as will be understood by those skilled in the art, adapted to be moved in the X-Y plane, for example, using stepper or DC motors (not shown) in response to the control signal to position the bracket body 47 in electrical discharge contact with the traveling wire electrode 117 to thereby perform the cutting pattern to form the bracket slot 51, 53. According to another embodiment of the present invention, the supply and take-up guides 125, 127, are moved in response to the control signal in the X-Y plane, for example, using stepper or DC motors (not shown), as will be understood by those skilled in the art, to position the traveling wire electrode 117 to perform the cutting pattern. According to an embodiment of the present invention, the supply guide 125 or the take-up guide 127 can further be positioned independently to thereby allow for the formation of various geometric shapes having non-parallel, non-planer surfaces. Note, the traveling wire electrode 117 via one or both of the guides 125, 127, or via the drive table 129 can also simultaneously separate the bracket body 47 from the runner 83 in response to the control signal.

As shown in FIG. 11, the electrode assembly 115 of an electrical discharge device 111' utilizing a die-sinker electrical discharge electrode 119 can include a ram (not shown) to extend the electrode adjacent the body of the bracket 45 when executing a hole formation portion of a cutting pattern to form the bracket slot 53. Note, rather than use a specific die-sinker electrode 119, a portion of the traveling wire electrode 117 disconnected from the take-up reel 125 can instead be used to function as a die-sinker electrode. Note, according to embodiments of the present invention other manufacturing methodologies including, for example, drilling a starter hole through the bracket body 47 or forming a starter hole through the bracket body 47 as part of the molding process, are within the scope of the present invention. Regardless of the methodology used to form the initial hole, once the initial hole has been formed through the bracket body 47, the end of the traveling wire electrode 117 can be connected to the take-up reel 125 to thereby function as described above in order to form a bracket slot 53 in the form of a tube, described later.

Figure 12:
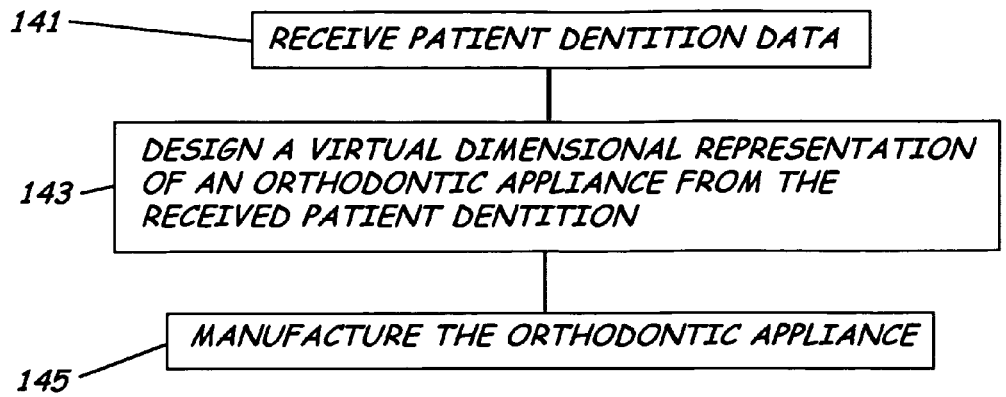
FIG. 12 is a flow diagram of a method of manufacturing an orthodontic appliance according to an embodiment of the present invention.

As shown in FIGS. 1-27, embodiments of the present invention also include methods of manufacturing orthodontic appliances. For example, as shown in FIG. 12, according to an embodiment of the present invention, a method of fabricating orthodontic appliances can include receiving patient dentition data (block 141) obtained through, for example, examination/diagnosis of a malocclusion using techniques known to those skilled in the art, designing a virtual dimensional representation of an orthodontic appliance from the received patient dentition (block 143), then manufacturing the orthodontic appliance (block 145). For example, an orthodontist or other medical professional performs an examination of a patient at the orthodontist's office to assemble data necessary to determine the patient's condition, prescribe the appropriate treatment, and specify the characteristics of the orthodontic appliance to implement the treatment. A physical model including a mandibular model and a maxillary model of the patient's lower and upper jaw, respectively, can be formed using a physical mold to be used to form a virtual model. Alternatively, a virtual model can be directly formed using various scanning techniques. Regardless of the methodology employed, a virtual model along with a prescription setting forth the treatment to be applied to the patient and a result to be achieved by the treatment can be used to form the dentition data. This data can be communicated to an appliance design and manufacturing facility where the design of the customized orthodontic appliance 41 can be carried out with the use of a computer, e.g., virtual orthodontic appliance design computer 31, a workstation, or other data processor known to those skilled in the art, which can store a three-dimensional virtual model of the patient's dentition the and treatment planning software or program product for moving the teeth in the virtual model to decide finish positions.

The orthodontic appliance 41 can include a customized archwire 43 and multiple precision customized brackets 45 each including a bracket body 47, bracket pad 49 connected to the bracket body 47, and a bracket slot 51, 53, in the bracket body 47. Various archwire forming systems and methods such as, for example, that described in U.S. Pat. No. 6,928,733 by Rubbert et al. titled "Method and System for Customizing an Orthodontic Archwire," incorporated herein by reference in its entirety, can be used to form a customized precision archwire 43 to be positioned in the bracket slots 51, 53, to form a precision interface which can provide in the bracket slot width dimension, for example, a combined tolerance of equal to or less than twenty microns and as low as approximately eight microns. The archwire 43 is typically formed of a stainless-steel, nickel-titanium based, titanium-niobium based, or titanium-molybdenum based alloys, but can be manufactured using various other materials known to those skilled in the art. The brackets 45 are typically formed of stainless-steel, titanium, or a titanium-based alloy, but can also be readily formed of various other materials known to those skilled in the art.

Various methodologies of forming the virtual bracket pad and bracket body can be employed. U.S. Pat. No. 6,776,614 by Wiechmann et al. titled "Modular System for Customized Orthodontic Appliances" incorporated herein by reference in its entirety, describes methodologies of designing a virtual dimensional representation of the orthodontic appliance 41 used to manufacture the brackets 45, including systems and methods of designing a customized orthodontic bracket 45 for an individual patient with the aid of a computer having access to a library of virtual descriptions of bracket features. For example, according to one methodology, bracket pad geometry can be derived directly from digital representations of the patient's teeth so as to produce a bracket bonding pad 49 that conforms substantially to the shape of the surface of the teeth. According to another methodology, described by Wiechmann et al., a software algorithm is employed that automatically or semi-automatically calculates an appropriate bracket bonding pad area by analyzing the curvature of the tooth surface and determines a surface that is large enough to cover substantial curvature features to allow for reliable manual positioning of the bracket 45 onto the tooth surface. Such an algorithm could for instance start with a pre-defined pad size. The tooth surface covered by that pad size would form a virtual "knoll" having at least one raised portion relative to surrounding tooth anatomy, as a completely flat tooth surface would not lend itself to unique positioning of a bracket. The volume of the knoll could be calculated provided that the edges of the pad are joined by a continuous surface in any convenient manner. The less curvature the tooth surface presents, the flatter the knoll and the smaller its volume would be. If the volume of the "knoll" does not exceed a pre-defined value, the pad would automatically be enlarged by a pre-defined value, with the idea that the larger volume would be more likely to include adequate raised tooth features. Again, the volume would be calculated. This loop would be continued until a minimum volume value would be achieved for each pad. This is just an exemplary approach for such an automated algorithm. Others could be readily chosen from the principles taught herein.

The portion of the bracket pads 49 away from the patient's teeth can also be designed to conform to the geometry of the patient's teeth. The bracket bodies 47 can also be designed and combined with the bracket pads 49. For example, a library of bracket bodies 47 is pre-created and stored in the computer to allow ready selection, however, the bracket bodies 47 can also be readily customized to meet the needs of the patient. The bracket slots 51, 53, can also be designed according to the needs of the patient. For example, the bracket slots 51, 53, can also be designed to align with the geometry of the patient's teeth. The bracket slots 51, 53, can be in the form of either an open end slot 51 extending into a surface of the bracket body or a closed end slot 53 forming a tube through the bracket body 47. Beneficially, using such manufacturing methodology, the tolerance along the bracket slot width 55 of either type of slot 51, 53, for example, can be less than thirty and as low as approximately eight microns corresponding to a calculated angle of rotation of only 0.7 degrees. This can be a significant improvement over that of the prior art which has tolerances as high as 40 microns for open end slots, and as high as between 40 to 100 microns for closed end slots. Such precision beneficially can result in a more predictable finishing process.

Further, other accessories such as, for example, bracket wings 57 or bracket hooks 59, can be integrated into the bracket design. Once the three-dimensional design of the bracket pad 49, bracket body 45, and other accessories are combined, the process is repeated for each bracket 45 forming the orthodontic appliance.

Figure 13:
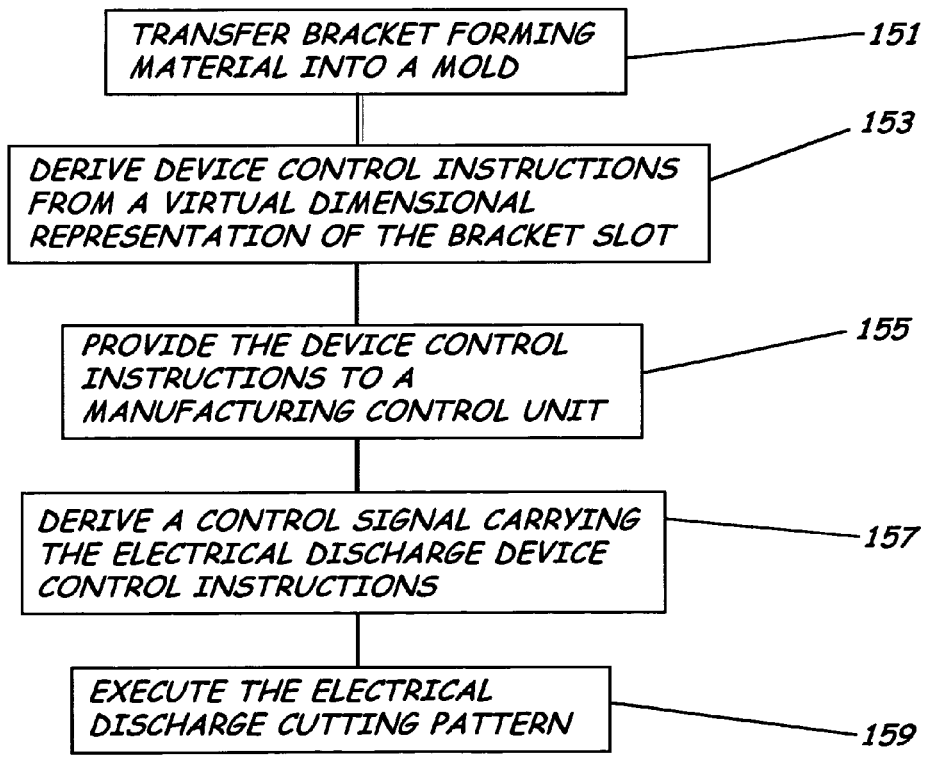
FIG. 13 is a flow diagram of a method of manufacturing an orthodontic appliance according to an embodiment of the present invention.
Figure 14:
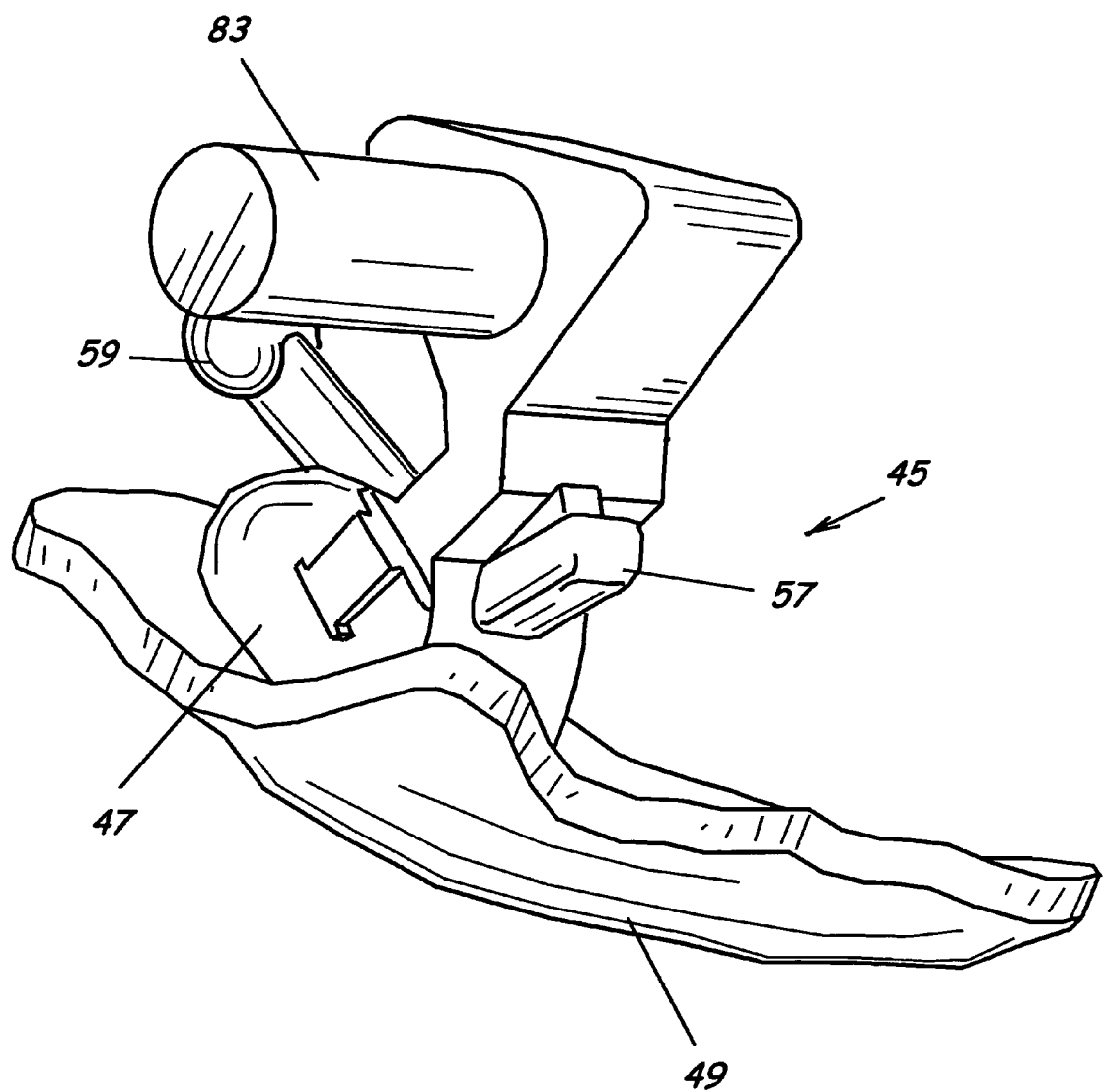
FIG. 14 is a perspective view of a bracket of an orthodontic appliance according to an embodiment of the present invention.
Figure 15:
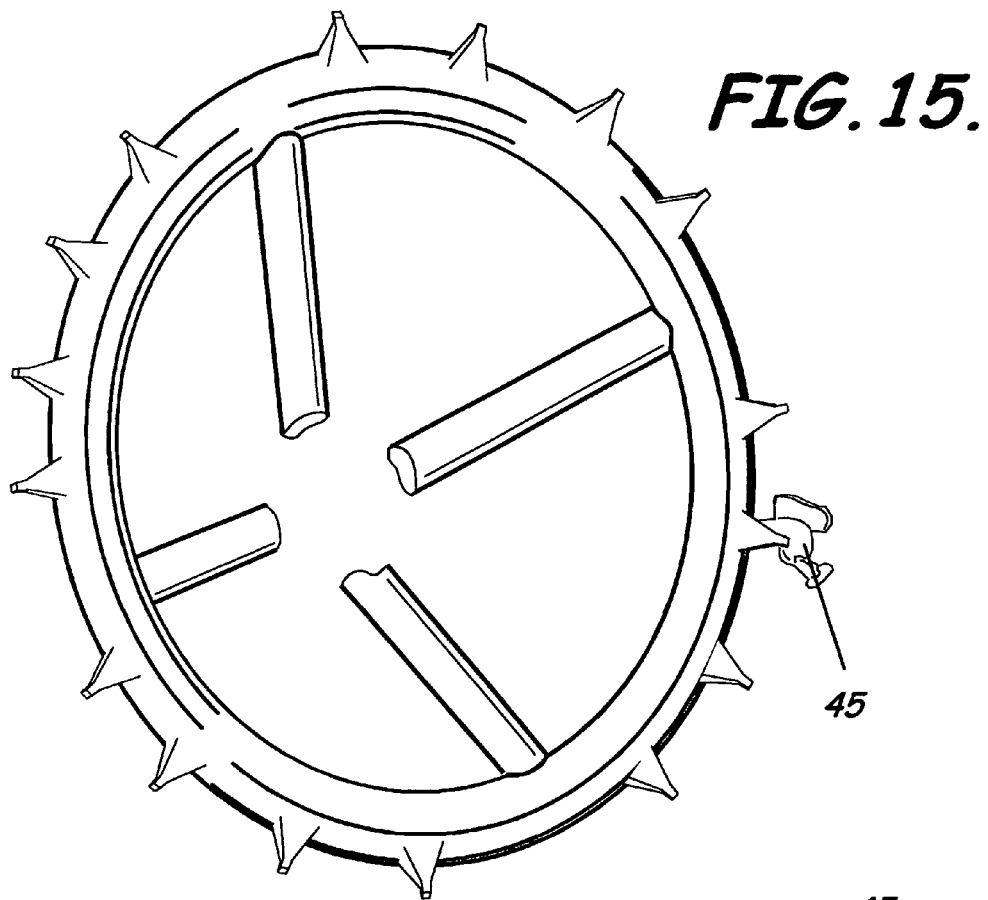
FIGS. 15-19 are perspective views of a portion of a molding apparatus and a molded bracket of an orthodontic appliance according to an embodiment of the present invention.
Figure 16:
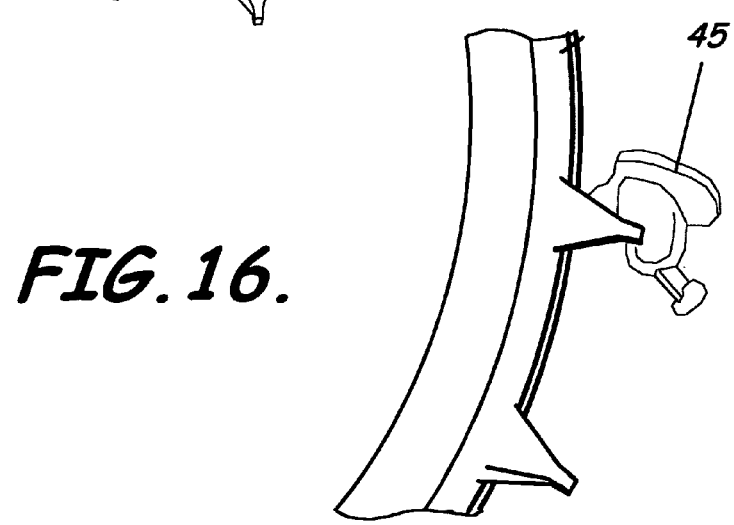
Figure 17:
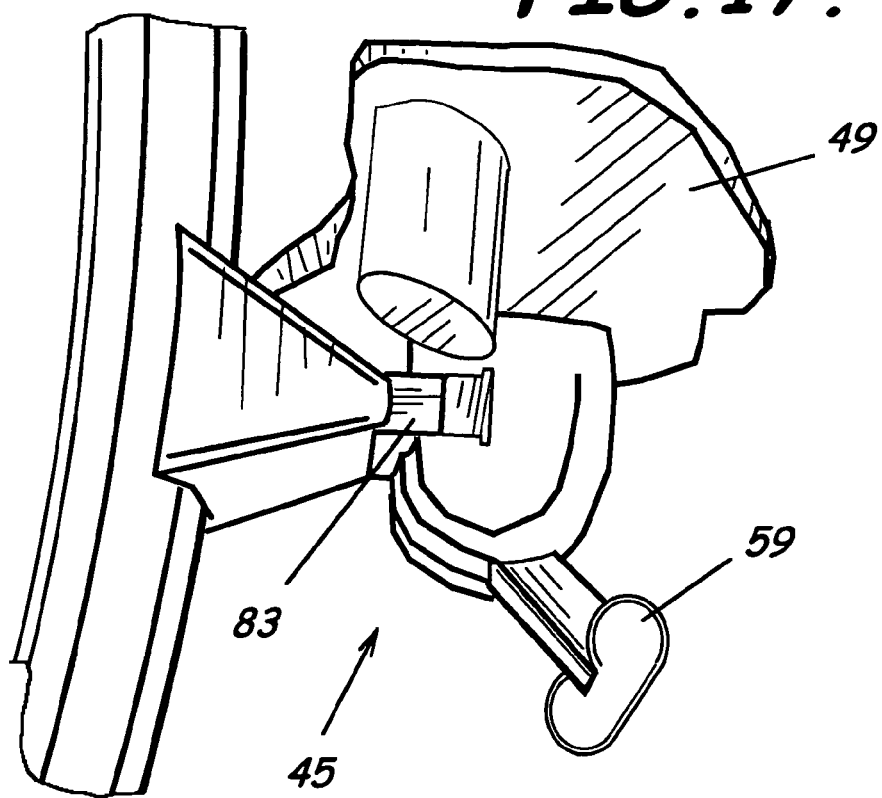
Figure 18:
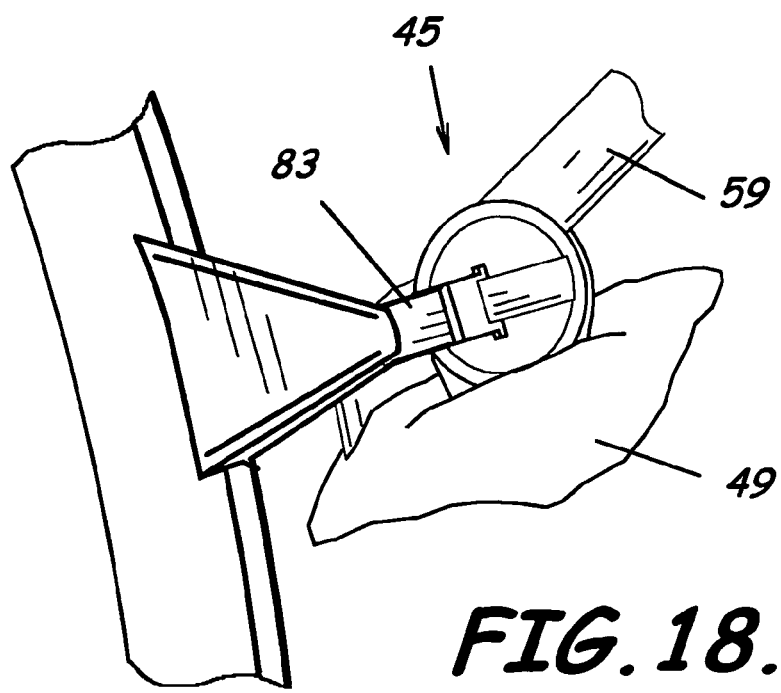
Figure 19:
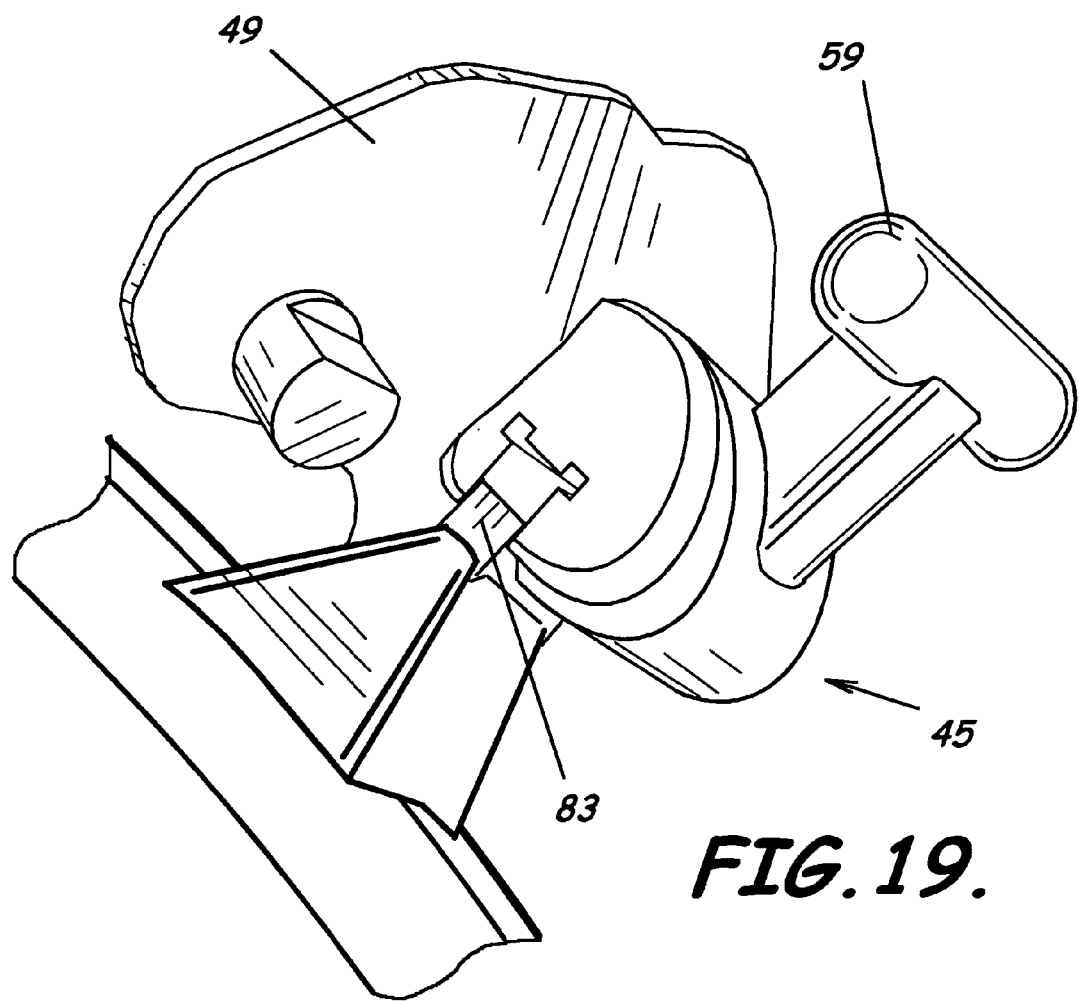

As shown in FIG. 13, according to an embodiment of the present invention, the method of manufacturing an orthodontic appliance can include using various molding techniques as known and understood by those skilled in the art. That is, the method can include pouring, injecting, or otherwise transferring bracket-forming material 75 into a mold 73 (block 151). The mold 73 (FIG. 8) can have a cavity 79 for each of the brackets 45 which defines peripheries of the bracket body 47 and bracket pad 49 when bracket-forming material 75 is positioned therein. Connected to each cavity 79 within the mold 73, for example, is a separate channel or sprue 81, which provides a separate conduit for the bracket-forming material 75 to be transferred into the respective cavity 79. Each channel 81 defines peripheries of a runner 83 when filled with the bracket material 75. According to an embodiment of the present invention, when the bracket-forming material 75 is solidified and when the brackets 45 are removed from the mold 73 each molded bracket body 47 remains connected to the runner 83 (see FIGS. 9 and 14-19). When the runners 83 are jointly connected, the runners 83 form what is often termed a mold tree.

According to an embodiment of the present invention, the method of manufacturing an orthodontic appliance can include using automated machining techniques. That is, a method of manufacturing an orthodontic appliance 41 can include deriving device control instructions, for example, using a data processing computer, e.g., data processing computer 91, including software or program product, e.g., computer-aided manufacturing program product 97 (FIG. 1), described previously, which can be used to formulate the device control instructions from the virtual dimensional representation of the bracket slot 51, 53, in the bracket body 47 (block 153). The device control instructions describe operations to execute a cutting pattern extending along a perimeter of the bracket slot 51, 53, that can be customized to substantially match associated dimensions of a preselected customized precision archwire 43, to thereby form a precision interface with the archwire 43. The device control instructions can be provided either manually or through a computer network, to a controller, e.g., controller 103, of a bracket manufacturing device, e.g., electrical discharge device 111, 111' (block 155). A control signal carrying the electrical discharge device control instructions are then derived (block 157) in response to the received electrical discharge device control instructions using, for example, the controller 103, carrying control program product 109. The electrical discharge cutting pattern is then executed in response to the control signals to form the bracket slot 51, 53 (block 159).

Figure 20:
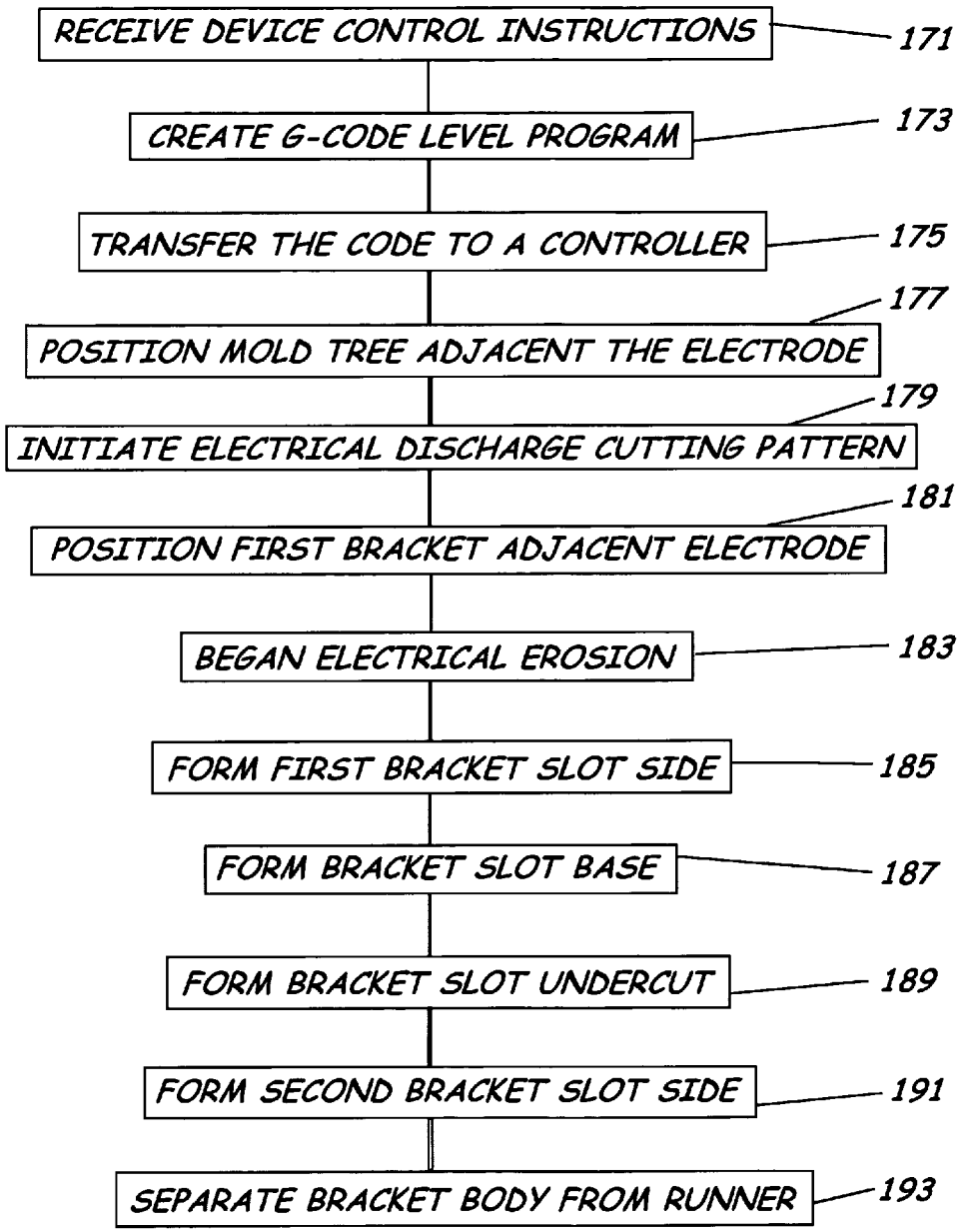
FIG. 20 is a flow diagram of a method of manufacturing an orthodontic appliance according to an embodiment of the present invention.
Figure 21:
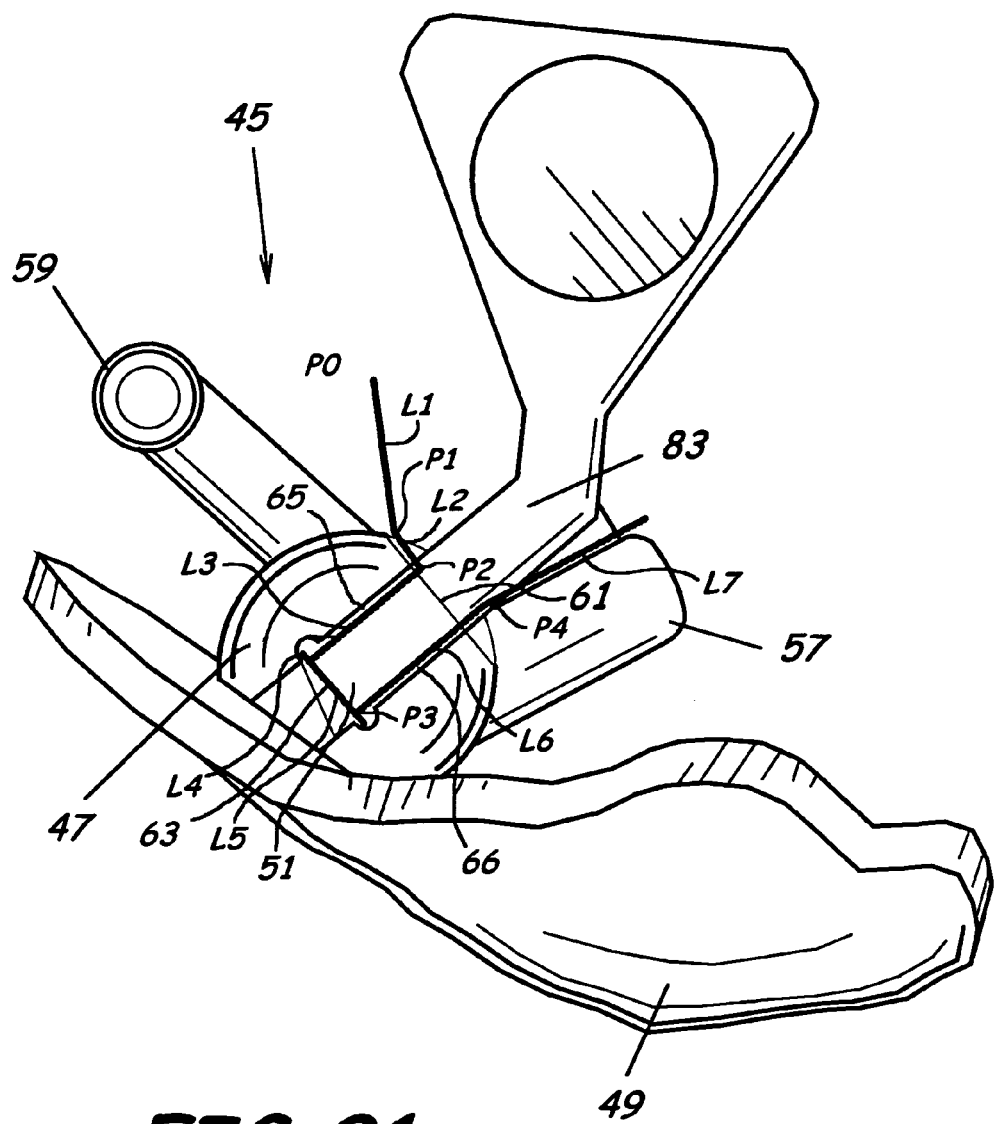
FIG. 21 is a perspective view of a bracket of an orthodontic appliance overlaid with a bracket slot cutting pattern according to an embodiment of the present invention.
Figure 22:
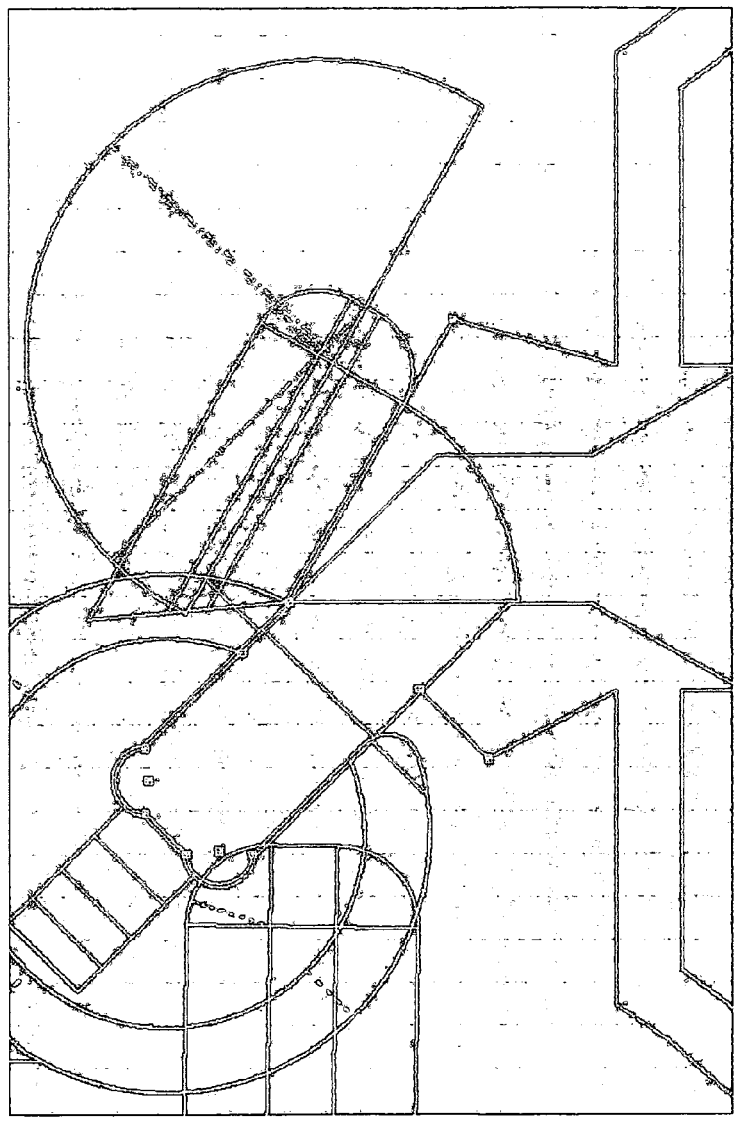
FIG. 22 is a schematic diagram of a bracket of an orthodontic appliance overlaid with a bracket slot cutting pattern according to an embodiment of the present invention.

As shown in FIG. 20, according to an embodiment of the present invention where the bracket slot is an open ended bracket slot 51 a method of manufacturing orthodontic appliances 42 can include executing the electrical discharge cutting pattern responsive to the control signal to form the bracket slot as illustrated in FIGS. 21 and 22. In the open-end bracket slot configuration, the bracket slot 51 has an open end 61, a closed base end 63, and two spaced-apart sides 65, 66, extending between the base end 63 and the open-end 61, and, for example, can be formed to accommodate being oriented parallel to the inner surface of the tooth so that the bracket is positioned upon and/or aligned according to the general orientation of the bracket pad 49. That is, the bracket slot 51 can be oriented substantially parallel to an orientation of the surface of the tooth, bracket pad geometry, or both. Similarly, according to an embodiment of the present invention, the bracket body 47 can have a shape substantially coinciding with the shape of an associated tooth.

According to an embodiment of the present invention, the bracket slot 51 is "cut" into the bracket body 47 using an electrical discharge apparatus 101 including an electrical discharge device 111 equipped with a traveling wire electrode 117 (see FIG. 10). An electrical discharge apparatus controller 103 receives device control instructions either directly from the user or through a communication link to a data processing computer 91 or system providing device control instructions describing movements of the electrode 117 or the brackets 45 to form the electrical discharge pattern (block 171). For example, the data processing computer 91 can have computer aided manufacturing program or code 97, which can receive input either from a virtual orthodontic device design computer 31 including an orthodontic design program or from some other form of computer aided design program, or can receive input from or an orthodontic design program or other computer-aided design program resident with the computer aided manufacturing program in the data processing computer 91, itself. According to an embodiment of the present invention, the computer aided manufacturing program 97 can be used to form device control instructions, e.g., computer numerical control program, similar to that created using manual operator programming, e.g., G-code level program such as that illustrated in FIG. 23, (block 173), as understood by those skilled in the art. As stated above, this code can be readily transferred to the electrical discharge apparatus controller 103 to control processing the electrical discharge cutting pattern (block 175).

Post-molding, the brackets 45 can be configured in the form of a mold tree connected via runners 83. After removing the brackets 45 from the mold 73, each of the brackets 45 and associated runners 83 are positioned on an electrical discharge apparatus drive table to have a bracket slot "cut" into the bracket body of each bracket and to be removed from the mold tree. After positioning the mold tree adjacent the electrode 117 (block 177), the electrical discharge cutting pattern can be initiated (block 179). Initiation of the pattern can be either manually through an operator of the electrical discharge apparatus or automatically through use of sensors as known to those skilled in the art. According to an embodiment of the present invention, an electrical discharge apparatus drive table 129 carrying the mold tree can individually position each bracket body 47 in electrical discharge contact with the traveling wire electrode 117. According to another embodiment of the present invention, this is accomplished via movement of the associated guides 125, 127.

Upon initiating the electrical discharge cutting pattern, the first bracket 45 on the mold tree is positioned so that the first bracket 45 is in the proper juxtaposition with the traveling wire electrode 117 at a starting point, e.g., start point $P_0$ shown in FIG. 21 (block 181), which is related to the program zero point of the apparatus 101 as known by those skilled in the art. Additionally, the supply reel 121 containing unused portions of the traveling wire electrode 117 begins providing a continuous stream of supply traveling wire electrode 117 and the take-up reel 123 containing used portions of the traveling wire electrode 117 begins collecting the traveling wire electrode 117 supplied from the supply reel 121. High frequency electrical current is also passed through the traveling wire electrode 117 and a dielectric fluid (not shown) is supplied so that the voltage in a gap between the traveling wire electrode 117 and the bracket body 47 can ionize the dielectric fluid and allow the "spark" to perform the eroding process on the bracket body 47 to form the bracket slot 51.

According to an embodiment of the present invention, in response to the drive control instructions, the drive table 129, and thus the bracket body 47, is positioned to translate the bracket 45 according to the first leg $L_1$ of the cutting pattern so that the traveling wire electrode 117 electrically engages but does not directly contact the bracket body 47. At point $P_1$, the electrode 117 is in electrical engagement with the bracket body 47 and the erosion process begins (block 183), melting or vaporizing a portion of the surface of the bracket 45. The bracket body 47 is then translated along leg $L_2$ until reaching the desired beginning point $P_2$ of the first side 65 of the bracket slot 51. Effectively, this initial portion of the pattern, particularly the second leg $L_2$, can extend the cutting pattern along a portion of an outer surface of the bracket body 47 substantially transverse to the first side 65 and into a portion of the runner 83.

The bracket body is then translated along leg $L_3$ until reaching the desired depth within the bracket body 47, forming the length of the first side 65 (block 185). The bracket body 47 is then translated along leg $L_4$ until reaching the desired transverse depth within the bracket body 47 forming a transverse extension extending into the bracket body from first side. The bracket body 47 is then retracted along leg $L_4$ and translated along leg $L_5$ until reaching the desired transverse depth within the bracket body 47 forming the bracket slot base 63 and forming a transverse extension extending into the bracket body from second side 66 (block 187). The bracket body 47 is then retracted along leg $L_5$ until reaching the desired beginning point $P_3$ within the bracket body to begin forming the second side 66. The transverse extensions extending beyond the first and second sides 65, 66, form a bracket slot undercut 67 (block 189). The bracket body 47 is then translated along leg $L_6$ until reaching a bracket slot cutting pattern ending point $P_4$ generally positioned adjacent to the beginning point $P_1$ of the first side 65 forming the length of the second side 66 (block 191). Note, although shown as parallel, the first and the second sides 65, 66, can form an acute angle with the base 63 of the bracket slot 51 so that the two spaced-apart sides 65, 66, converge extending from the bracket slot base 63 to the bracket slot opening 61 or from the bracket slot opening 61 to the bracket slot base 63.

The bracket body 47 is then translated along leg $L_7$ until exiting the runner 83, effectively separating the bracket body 47 from the runner 83 and thus, from the mold tree (block 193). If the bracket body design includes a bracket wing 57 such as that illustrated in FIGS. 4 and 21, the bracket body 47 is further translated so that the cutting pattern extends along the slot-side surface of the bracket wing 57 to thereby form the slot-side surface of the bracket wing 57, separating the bracket body 47 from the runner 83. Note, as described previously, rather than translate the bracket body 47, the guides 125, 127, can be translated to perform the operations described above and those described below.

Figure 24:
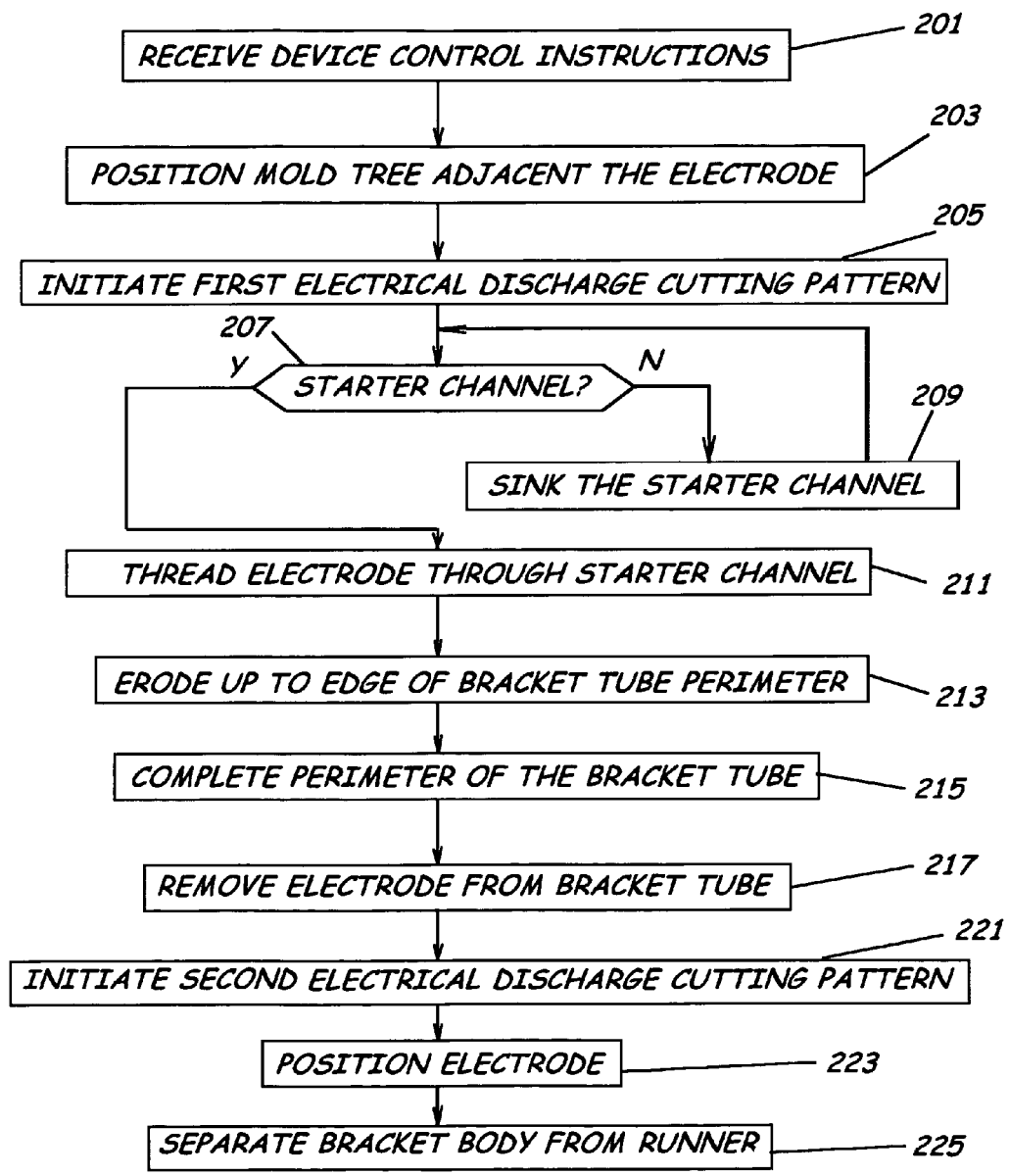
FIG. 24 is block flow diagram of a method of manufacturing and orthodontic appliance according to an embodiment of the present invention.
Figure 25:
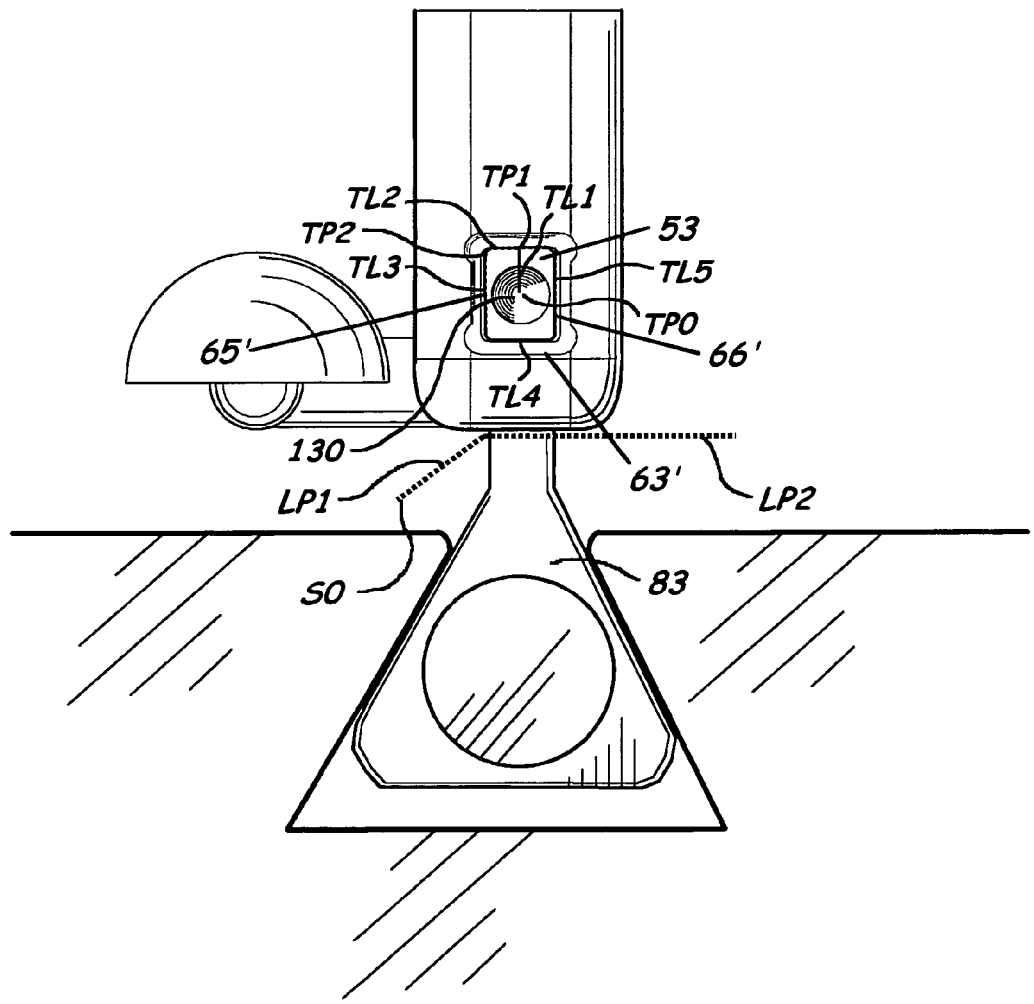
FIG. 25 is a perspective view of a bracket of an orthodontic appliance overlaid with a bracket slot cutting pattern according to an embodiment of the present invention.
Figure 26:
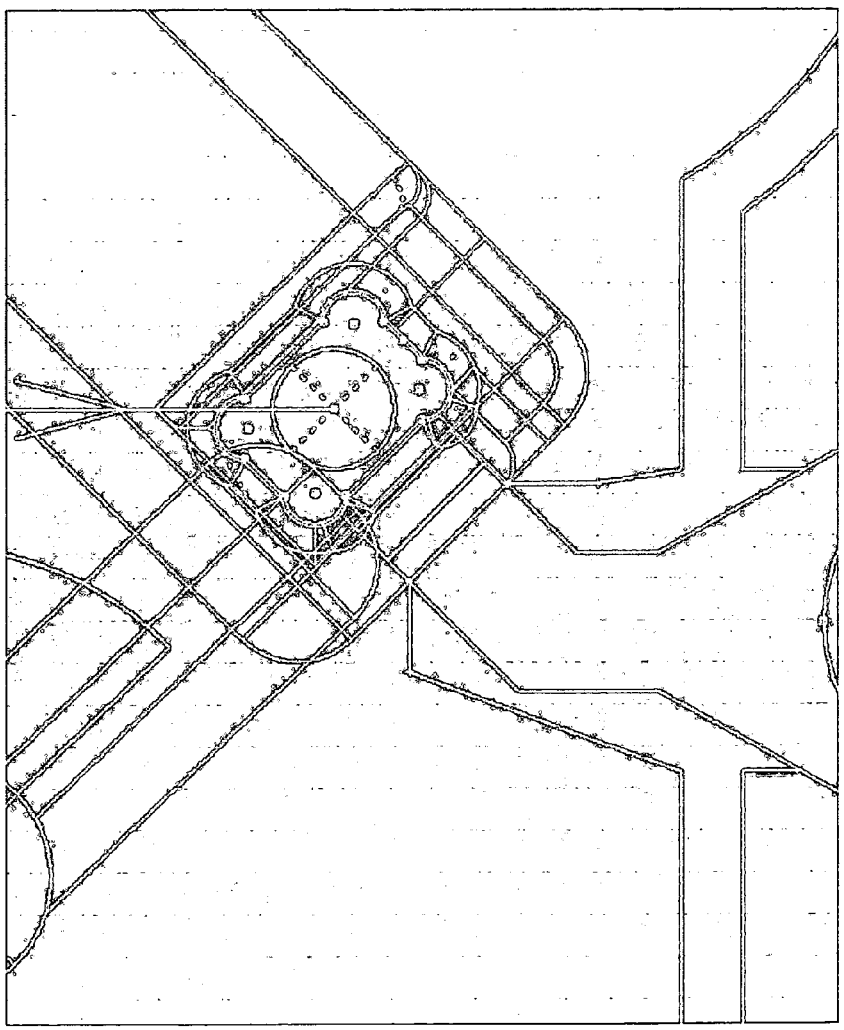
FIG. 26 is a schematic diagram of a bracket of an orthodontic appliance overlaid with a bracket slot cutting pattern according to an embodiment of the present invention.

As shown in FIG. 24, according to an embodiment of the present invention where the bracket slot is a closed ended bracket slot 53 defining a channel or tube through the bracket body 47, a method of manufacturing orthodontic appliances 41 can include executing the electrical discharge cutting pattern in response to the control signal to form the bracket slot as illustrated in FIGS. 25 and 26. In the tubular bracket slot configuration, the bracket slot 53 has a closed perimeter and extends through the bracket body 47. The tubular bracket slot 53, similar to the open-ended bracket slot 51 can also, for example, be formed to accommodate being oriented parallel to the inner surface of the tooth so that the bracket body 47 is positioned upon and/or in the general orientation of the bracket pad 49. That is, the bracket slot 53 can be oriented substantially parallel to an orientation of the surface of the tooth, bracket pad geometry, or both. Similarly, the bracket body 47 carrying the bracket slot 53 having the tubular shape can also have a shape substantially coinciding with the shape of an associated tooth.

According to an embodiment of the present invention, in response to the control signal a first electrical discharge cutting pattern is executed to form the bracket tube 53. The pattern extends along a perimeter of the bracket tube 53 and can be customized to substantially match associated dimensions of a preselected archwire 43 to thereby form a precision interface with the archwire 43. The bracket tube 53 is "cut" into the bracket body 47 using, for example, a combination die-sinker electrode 119 and a traveling wire electrode 117. The electrical discharge apparatus controller 103, as described previously, can receive device control instructions such as, for example, those illustrated in FIG. 27, either directly from the user or through a communication link to a data processing computer 91 or system providing device control instructions describing movements of the electrodes to form the electrical discharge pattern (block 201). Alternatively, a starter hole can be preformed through other means known to those skilled in the art. After positioning the mold tree (block 203), the electrical discharge cutting pattern can be initiated (block 205) either manually through an operator of the electrical discharge apparatus 101 or automatically through use of sensors, as known to those skilled in the art.

Upon initiating the electrical discharge cutting pattern, the first bracket 45 on the mold tree requiring a tube to be cut therethrough is positioned so that the bracket is in the proper juxtaposition with the traveling wire electrode 117 at a starting point, e.g., start point $TP_0$ shown in FIG. 25, which can be related to the program zero point of the electrical discharge device 111'. If a starter channel 130 has not previously been formed (block 207), a die-sinker electrode 119 or a disconnected piece of the traveling wire electrode 117 can be used to form or sink the starter channel 130 (block 209). High frequency electrical current is passed through the electrode 117, 119, and the dielectric fluid is supplied so that the voltage in a gap between the electrode 117, 119, and the bracket body 47 can ionize the dielectric fluid to perform the eroding process on the bracket body 47 to form the starter channel for the bracket tube 53. After sinking the channel 130 to accommodate normal deployment of the traveling wire electrode 117, the traveling wire electrode 117 is threaded through the channel 130 at the starting point $TP_0$ (block 211). The supply reel 121 containing unused portions of the traveling wire electrode 117 begins providing a continuous stream of supply traveling wire electrode 117 and the take-up reel 123 containing used portions of the traveling wire electrode 117 begins collecting the traveling wire electrode 117 supplied from the supply reel 121 at a user selected or material dependent rate. As described previously, high frequency electrical current is also passed through the traveling wire electrode 117 and the dielectric fluid is supplied to perform the eroding process on the bracket body 47 to form the bracket tube.

According to a preferred embodiment of the present invention, in response to the drive control instructions, the bracket body is translated according to the first leg $TL_1$ of the cutting pattern so that the traveling wire electrode 117 electrically erodes bracket body material up to a portion of the desired perimeter of the bracket tube 53 (block 213), for example, at initial perimeter starting point $TP_1$. The bracket body 47 is then translated along leg $TL_2$ until reaching the desired beginning point $TP_2$ of the first side 65'. The bracket body 47 is then translated along leg $TL_3$ until reaching the desired length of the bracket tube 53. The bracket body 47 is then translated along leg $TL_4$ until reaching the desired width 55' of the bracket slot 53. The bracket body 47 is then translated along leg $TL_5$ until reaching the desired length of the second side 66'. The bracket body 47 is then translated until reaching the initial perimeter starting point $TP_1$, completing the perimeter of the bracket slot 53 (block 215). The traveling wire electrode 117 is then removed from within the bracket tube 53 (block 217). Note, although shown as parallel, the first and second sides 65', 66', can form an acute angle with the bracket slot base 63' of the slot 53 so that the two spaced-apart sides 65', 66', converge extending either from the bracket slot base 63' or toward the bracket slot base 63'. Further, similar to the open-ended bracket slot 51, described previously, either the length or width of one or more of the legs can be extended so that the length of the cut exceeds the length or width of the bracket tube 53 to thereby form an undercut.

According to an embodiment of the present invention, in response to the control signal, a second electrical discharge cutting pattern can also be executed to separate the bracket body 47 from the runner 83 (see FIGS. 25-27). Upon initiating the second electrical discharge cutting pattern (block 221), the bracket body 47 is repositioned so that the bracket 45 is in the proper juxtaposition with the traveling wire electrode 117 (block 223) at a starting point, e.g., start point $S_0$ shown in FIG. 25. The bracket body 47 is then repositioned according to the first leg $LP_1$ of the cutting pattern. The bracket body 47 is then translated along leg $LP_2$ until exiting the runner 83, effectively separating the bracket body 47 from the runner 83 (block 225) and thus, from the mold tree.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links.

As shown in FIGS. 1-27, embodiments of the present invention include a computer readable medium that is readable by a computer to fabricate or manufacture orthodontic appliances. For example, according to an embodiment of the present invention, provided is a computer readable medium containing a set of instructions that, when executed by the computer, cause the computer to perform the operation of receiving a virtual dimensional representation of a bracket slot 51, 53, in a bracket body 47 of a bracket 45 of an orthodontic appliance 41, and deriving device control instructions in response to the virtual dimensional representation of a bracket slot 51, 53, and/or user input. The device control instructions include those to perform the operation of executing an electrical discharge cutting pattern extending along a perimeter of the bracket slot 51, 53, with sufficient precision to substantially match associated dimensions of a preselected archwire 43 to thereby form a precision interface with the archwire 43.

Specifically, for an open-ended slot 51, as perhaps best shown in FIG. 21, the device control instructions, for example, can include those to perform the operations of detecting or determining a position on a bracket body 47 defining a cutting pattern starting point to begin electrical discharge machining, extending an initial portion of the cutting pattern along a portion of an outer surface of the bracket body adjacent the mouth of the slot 51, cutting a path extending into the bracket body 47 to form a first side 65 of the slot 51, cutting a path extending at least partially transverse to the first side 65 to form a bracket base end 63, and extending the cutting path to the surface of the bracket body 47 to form the second side 66 and to complete formation of the bracket slot 51. The instructions can also include those to perform the operation of forming a transverse extension extending into the bracket body 47 from one or both of the spaced-apart sides 65, 66, adjacent the base end 63 of the bracket slot 51 to thereby form a bracket slot undercut 67. The instructions can also include those to perform the operation of extending a portion of the cutting pattern along the slot-side surface of the bracket wing 57 to thereby form the slot-side surface of the bracket wing 57. Advantageously, according to embodiments of the present invention, the cutting pattern is selected so that the completion of the bracket slot 51 or completion of cutting the slot-side surface of the bracket wing 57, if applicable, results in severance of the bracket body 47 from an associated runner 83.

For a closed-ended slot 53, as perhaps best shown in FIG. 25, the device control instructions, for example, can include those to perform the operations of detecting or determining a position on a bracket body 47 defining a first cutting pattern starting point to begin electrical discharge machining, extending an initial portion of the cutting pattern to a point adjacent the inner perimeter of the bracket slot 53, and extending the cutting pattern along the inner perimeter of the bracket slot 53 to thereby form the bracket slot 53. The instructions can also include those to perform the operation of forming a transverse extension extending into the bracket body 47 from one of the sides 65', 66', adjacent the base end 63' of the bracket slot 53 to thereby form a bracket slot undercut. Note, for bracket bodies 47 lacking a pre-formed starter channel 130, the instructions can also include those to perform the operation of forming the starter channel 130. The instructions can also include those to perform the operations of detecting or determining a position on a bracket body 47 defining a second cutting pattern starting point to begin electrical discharge machining and extending the second cutting pattern through a runner 83 to thereby sever the bracket body 47 from the runner 83.

According to embodiments of the present invention, provided is a computer readable medium containing a set of instructions that, when executed by the computer, cause the computer to perform the operation of receiving electrical discharge device control instructions describing a virtual dimensional representation of a bracket slot 51, 53, in a bracket body 47 of a bracket 45 of an orthodontic appliance 41, and deriving a control signal carrying the electrical discharge device control instructions responsive to the electrical discharge device control instructions to perform the above described operations.

This application is related to U.S. Provisional Application No. 60/763,022, filed on Jan. 27, 2006, incorporated herein by reference in its entirety.

The invention has been described in considerable detail with specific reference to these illustrated embodiments. It will be apparent, however, that various modifications, alterations, and other changes can be made within the spirit and scope of the invention as described in the foregoing specification. For example, the slot-less bracket was described as produced within a mold. Other methodologies of producing the pre-processed bracket are within the above teachings. Further, for example, the bracket slot was described as being formed according to device control instructions. In an alternative embodiment of the present invention, other machining methodologies including mailing, drilling, turning, honing, ultrasonic machining, high-pressure water cutting or grinding, known to those skilled in the art, alone or in combination with themselves, or with electrical discharge machining, can be used to execute the above described machining pattern extending along a perimeter of the bracket slot to provide a customized bracket slot formed to substantially match associated dimensions of an archwire.

Additionally, insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. Further, the words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim shall be understood as being generic to all possible meanings supported by the specification and by the word itself.

In the drawings and specification, there have been disclosed embodiments of the invention, and although specific terms are employed, the terms are used in a descriptive sense only and not for purposes of limitation, the scope of the invention being set forth in the following claims.

That claimed is:

1. A system to manufacture orthodontic appliances, the system comprising:
 a virtual orthodontic appliance design computer having a processor, memory coupled to the processor, and orthodontic appliance design program product stored in the memory including instructions to perform operations of receiving patient dentition data and designing a virtual dimensional representation of an orthodontic appliance defining virtual orthodontic appliance design data responsive to the received patient dentition data, the orthodontic appliance including a customized archwire and a plurality of precision customized brackets each including a tooth facing bonding surface and a bracket slot;
 a mold forming apparatus positioned to form each bracket including a mold positioned to receive a bracket-forming material and a dispensing device positioned to dispense the bracket-forming material into the mold, the mold having a cavity for each of the plurality of brackets defining peripheries of the bracket when the bracket-forming material is positioned therein and having a channel defining peripheries of a runner when filled with the bracket-forming material, each molded bracket connected to the runner when removed from the mold;
 a data processing computer in conununication with the virtual orthodontic appliance design computer and having memory and computer-aided manufacturing program product stored in the memory including instructions that when executed by the data processing computer cause the data processing computer to perform an operation of deriving electrical discharge device control instructions including those to perform an operation of forming a pattern describing a virtual dimensional representation of the bracket slot responsive to the virtual orthodontic appliance design data, and including those to perform an operation of simultaneously separating the bracket from the runner when forming the bracket slot; and
 an electrical discharge machining apparatus in communication with the data processing computer and comprising:
  a controller having memory and data communication program product stored in the memory including instructions that when executed by the controller cause the controller to perform an operation of receiving the electrical discharge device control instructions, and having control program product also stored in the memory and including instructions that when executed by the controller cause the controller to derive a control signal carrying the electrical discharge device control instructions responsive to the received electrical discharge device control instructions, and
  an electrical discharge device comprising an electrical discharge electrode assembly including an electrode and at least one drive section adapted to position each bracket in electrical discharge contact with the electrode to form the bracket slot and adapted to simultaneously separate the bracket from the runner when forming the bracket slot responsive to the control signal.

2. A system as defined in claim 1, wherein the electrical discharge device control instructions include those to perform an operation of executing an electrical discharge cutting pattern extending along a perimeter of the bracket slot.

3. A system as defined in claim 2, wherein the bracket slot includes an open surface end and a closed base end and two spaced-apart sides extending therebetween, and wherein an initial portion of the cutting pattern extends along a portion of an outer surface of the bracket substantially transverse to at least one of the sides.

4. A system as defined in claim 2, wherein the bracket slot includes an open surface end and a closed base end and two spaced-apart sides extending therebetween, wherein the bracket includes a bracket wing having slot-side surface, and wherein a portion of the cutting pattern extends along the slot-side surface of the bracket wing to thereby form the slot-side surface of the bracket wing.

5. A system as defined in claim 2, wherein the bracket slot includes an open end and a closed base end and two spaced-apart sides extending therebetween, and wherein a portion of the cutting pattern includes a transverse extension extending into the bracket from one of the spaced-apart sides at the base end of the bracket slot to thereby define a bracket slot undercut.

6. A system as defined in claim 2, wherein the bracket slot includes an open end and a closed base end and two spaced-apart sides extending therebetween spaced apart to define a bracket slot width, and wherein a portion of the cutting pattern includes at least one transverse extension extending into the bracket from a corresponding at least one of the spaced-apart sides adjacent the base to thereby define a bracket slot undercut having an undercut width, the undercut width exceeding the bracket slot width.

7. A system as defined in claim 2, wherein the electrical discharge device control instructions include those to perform an operation of detecting a position on a bracket defining a cutting pattern starting point to begin electrical discharge machining.

8. A system as defined in claim 2, wherein the electrode includes a traveling wire electrical discharge electrode defining a traveling wire electrode, wherein the electrode assembly includes a supply reel containing unused portions of the traveling wire electrode to provide a continuous stream of supply traveling wire electrode when executing the cutting pattern and a take-up reel containing used portions of the traveling wire electrode to collect the traveling wire electrode supplied from the supply reel when executing the cutting pattern to form the bracket slot and to provide tension to the traveling wire electrode to thereby provide a substantially planer cutting surface, wherein the bracket slot and the archwire form a bracket slot-archwire interface when the archwire is positioned within the bracket slot, and wherein the bracket slot-archwire interface provides in at least one dimension a tolerance of equal to or less than approximately 20 microns.

9. A system as defined in claim 2, wherein the electrode includes a die-sinker-electrical discharge electrode, wherein the electrode assembly includes a ram to extend the electrode adjacent the bracket when executing the cutting pattern to form the bracket slot, and wherein the bracket slot is specified having at least in one dimension a tolerance of less than 30 microns.

10. A system to manufacture orthodontic appliances, the system comprising:
a numerical control data processor defining a controller having memory and control program product stored in the memory including instructions that when executed by the controller cause the controller to perform an operation of deriving a numerical control signal carrying electrical discharge device control instructions to form a bracket slot in a bracket of an orthodontic appliance having a runner connected thereto and to separate the bracket from the runner connected to the bracket; and
an electrical discharge device in communication with the controller and having an electrical discharge electrode assembly including an electrode and having at least one drive section adapted to position the bracket in electrical discharge contact with the electrode responsive to the numerical control signal to form the bracket slot and to separate the bracket from the runner when forming the bracket slot.

11. A system to manufacture orthodontic appliances, the system comprising:
a numerical control data processor defining a controller having:
memory,
data communication program product stored in the memory including instructions that when executed by the controller cause the controller to perform an operation of receiving electrical discharge device control instructions describing a virtual dimensional representation of a custom bracket slot in a bracket of an orthodontic appliance, the custom bracket slot having dimensions substantially matching associated dimensions of a custom archwire, the dimensions of the custom bracket slot sized to substantially match the associated dimensions of the custom archwire to thereby form a precision interface with the custom archwire to minimize torque error, the custom bracket slot further having two spaced-apart sides spaced apart to define a bracket slot width and a base end extending therebetween, the electrical discharge device control instructions including those to perform the operation of forming a transverse extension extending into the bracket from one of the spaced-apart sides at the base end of the bracket slot to thereby define a bracket slot undercut having an undercut width, the undercut width exceeding the bracket slot width, and
control program product also stored in the memory including instructions that when executed by the controller cause the controller to perform an operation of deriving a control signal carrying the electrical discharge device control instructions responsive to the electrical discharge device control instructions; and
an electrical discharge device in communication with the controller having an electrical discharge electrode assembly including an electrode and having at least one drive section adapted to position the bracket in electrical discharge contact with the electrode responsive to the control signal to form the bracket slot and the bracket slot undercut.

12. A system as defined in claim 11, wherein the bracket is connected to a runner when formed, and wherein the electrical discharge device control instructions include those to perform an operation of executing the electrical discharge cutting pattern extending along a perimeter of the bracket slot to form the bracket slot and to simultaneously separate the bracket from the runner when forming the bracket slot responsive to the control signal.

13. A system as defined in claim 12, wherein the bracket slot includes an open surface end and a closed base end and two spaced-apart sides extending therebetween, and wherein the electrical discharge device control instructions include those to perform an operation of extending an initial portion of the electrical discharge cutting pattern along a portion of an outer surface of the bracket substantially transverse to at least one of the sides.

14. A system as defined in claim 12, wherein the bracket slot includes an open surface end and a closed base end and two spaced-apart sides extending therebetween, wherein the bracket includes a bracket wing having a slot-side surface, and wherein the electrical discharge device control instructions include those to perform an operation of extending a portion of eletrical discharge cutting pattern along the slot-side surface of the bracket wing to thereby form the slot-side surface of the bracket wing.

15. A system as defined in claim 12, wherein the electrical discharge device control instructions include those to perform an operation of detecting a position on the bracket defining a cutting pattern starting point to begin electrical discharge machining.

16. A system as defined in claim 15, wherein the electrode includes a die-sinker-electrical discharge electrode, and wherein the bracket slot is a tube.

17. A system as defined in claim 12, wherein the electrode includes a wire-cut-electrical discharge electrode, and wherein the bracket slot is specified having at least in one dimension a tolerance of less than 30 microns.

18. A system as defined in claim 12, wherein the precision interface provides in at least one dimension a play or tolerance of equal to or less than approximately 20 microns.

19. A method of manufacturing orthodontic appliances, the method comprising the steps of:
  deriving a control signal carrying device control instructions from a virtual dimensional representation of a bracket slot in a bracket of an orthodontic appliance describing operations to execute an electrical discharge cutting pattern extending along a perimeter of the bracket slot and configured to substantially match associated dimensions of a custom archwire to thereby form a precision interface with the custom archwire when positioned therein, and to separate the bracket from a runner, the runner connected to the bracket prior to execution of the electrical discharge cutting pattern; and
  executing the electrical discharge cutting pattern responsive to the control signal to form the bracket slot.

20. A method as defined in claim 19, wherein the electrical discharge cutting pattern is customized to substantially match associated dimensions of a preselected archwire.

21. A method as defined in claim 19, wherein prior to executing the electrical discharge cutting pattern, the bracket is connected to the runner which is connected to a mold tree, and wherein the step of executing the electrical discharge cutting pattern includes the step of cutting the bracket from the mold tree.

22. A method as defined in claim 19, wherein the bracket slot includes an open surface end and a closed base end and two spaced-apart sides extending therebetween, and wherein the step of executing the electrical discharge cutting pattern further includes the step of forming a transverse extension extending into the bracket from one of the spaced-apart sides adjacent a close based end of the bracket slot to thereby define a bracket slot undercut.

23. A method as defined in claim 19, wherein the bracket slot includes an open surface end and a closed base end and two sides extending therebetween spaced apart to define a bracket slot width, and wherein the step of executing the electrical discharge cutting pattern further includes the step of forming a transverse extension extending into the bracket from one of the spaced-apart sides adjacent a closed based end of the bracket slot to thereby define a bracket slot undercut having an undercut width, the undercut width exceeding the bracket slot width.

24. A method as defined in claim 19, wherein the bracket includes a bracket wing, and wherein the step of executing the electrical discharge cutting pattern further includes the step of extending a portion of the electrical discharge cutting pattern along a slot-side surface of the bracket wing to thereby form the slot-side surface of the bracket wing.

25. A method as defined in claim 19, wherein the bracket slot includes an open surface end and a closed base end and two sides extending therebetween, and wherein the step of executing the electrical discharge cutting pattern further includes the step of extending an initial portion of the electrical discharge cutting pattern along a portion of an outer surface of the bracket substantially transverse to at least one of the sides.

26. A method as defined in claim 19, wherein the bracket slot has a bracket slot base and at least two spaced-apart sides, and wherein the step of executing the electrical discharge cutting pattern further includes the step of forming an acute angle between the one of the sides and the bracket slot base so that the two spaced-apart sides converge extending from the bracket slot base.

27. A method as defined in claim 19, wherein the bracket slot is a bracket tube; wherein the electrical discharge cutting pattern is a first electrical discharge cutting pattern, wherein prior to executing the first electrical discharge cutting pattern, the bracket is connected to a runner, and wherein the method further comprises the step of executing a second electrical discharge cutting pattern responsive to the control signal to separate the bracket from the runner.

28. A method as defined in claim 19, wherein the archwire is a customized archwire, and wherein the method further comprises the step of forming the customized archwire adapted to be positioned in the bracket slot to form a bracket slot-archwire interface providing in at least one dimension a play or tolerance of equal to or less than approximately 20 microns.

29. A method of manufacturing orthodontic appliances, the method comprising the steps of:
  deriving a control signal carrying device control instructions from a virtual dimensional representation of a custom bracket slot in a bracket of an orthodontic appliance describing operations to execute an electrical discharge cutting pattern extending along a perimeter of the custom bracket slot and configured to substantially match associated dimensions of an archwire to thereby form a precision interface with the archwire, the bracket slot having a closed perimeter to thereby define a bracket tube; and
  executing the electrical discharge cutting pattern responsive to the control signal to form the bracket tube.

30. A method as defined in claim 29, wherein the electrical discharge cutting pattern is a first electrical discharge cutting pattern, wherein prior to executing the first electrical discharge cutting pattern the bracket is connected to a runner, and wherein the method further comprises the step of executing a second electrical discharge cutting pattern responsive to the control signal to separate the bracket from the runner.

31. A method as defined in claim 29, wherein the electrical discharge cutting pattern is a first electrical discharge cutting pattern, wherein prior to executing the first electrical discharge cutting pattern, the bracket is connected to a runner which is connected to a mold tree, and wherein the method further comprises the step of executing a second electrical discharge cutting pattern responsive to the control signal to separate the bracket from the mold tree.

32. A method of manufacturing orthodontic appliances, the method comprising the steps of:
  deriving device control instructions from a virtual dimensional representation of a bracket slot in a bracket of an orthodontic appliance describing steps to execute an electrical discharge machining cutting pattern to form the bracket slot, the bracket slot having two spaced-apart sides spaced apart to define a bracket slot width and a closed base end extending therebetween, the electrical discharge machining cutting pattern extending along a perimeter of the bracket slot and forming a transverse extension extending into the bracket from one of the spaced-apart sides at the closed based end of the bracket slot to thereby define a bracket slot undercut having an undercut width, the undercut width exceeding the bracket slot width;
  deriving a control signal carrying the device control instructions; and
  executing the electrical discharge machining cutting pattern responsive to the control signal.

33. A method as defined in claim 32, wherein the transverse extension is a first transverse extension, and wherein the electrical discharge machining cutting pattern includes a second transverse extension into the bracket from the other one of the spaced apart sides at the base end of the bracket slot to thereby further define to bracket slot undercut.

34. A method as defined in claim 32, wherein a distance between the two spaced-apart sides adjacent the base end defines the bracket slot width, and wherein the undercut extends into the bracket at both of the spaced-apart sides at the base end of the bracket slot.

35. A method as defined in claim 32, wherein the orthodontic appliance includes a bracket bonding surface having a shape substantially coinciding with the shape of an associated tooth.

36. A method of manufacturing orthodontic appliances, the method comprising the steps of:
deriving a control signal carrying device control instructions describing operations to execute a machining cutting pattern to form a bracket slot and to substantially simultaneously separate a bracket of an orthodontic appliance from a runner connected thereto; and
executing the machining cutting pattern responsive to the control signal to include substantially simultaneously separating the bracket from the runner when forming the bracket slot.

37. A method as defined in claim 36, wherein machining includes electrical discharge machining.

38. A method as defined in claim 36,
wherein the step of deriving a control signal includes receiving a virtual dimensional representation of the bracket slot in the bracket; and
wherein the machining cutting pattern extends along a perimeter of the bracket slot.

39. A method as defined in claim 36, wherein prior to executing the machining cutting pattern, the bracket is connected to the runner which is connected to a mold tree, and wherein the step of executing the machine cutting pattern includes the step of cutting the bracket from the mold tree.

40. A system to manufacture orthodontic appliances, the system comprising:
a data processing computer in communication with a virtual orthodontic appliance design computer and having memory and computer-aided manufacturing program product stored in the memory including instructions that when executed by the data processing computer cause the data processing computer to perform an operation of deriving electrical discharge device control instructions responsive to virtual orthodontic appliance design data, the electrical discharge device control instructions including those to perform an operation of forming a pattern describing a virtual dimensional representation of a bracket tube in a bracket body of an orthodontic bracket;
a numerical control data processor defining a controller having memory and control program product stored in the memory including instructions that when executed by the controller cause the controller to perform an operation of deriving a numerical control signal carrying the electrical discharge device control instructions to detect a position on the bracket body defining a cutting pattern starting point of an electrical discharge cutting pattern to begin electrical discharge machining and to form the bracket tube in the bracket body of the orthodontic bracket according to the electrical discharge cutting pattern responsive to the received electrical discharge device control instructions; and
an electrical discharge device comprising an electrical discharge electrode assembly including an electrode and at least one drive section adapted to position the bracket body in electrical discharge contact with the electrode to execute the electrical discharge cutting pattern to form the bracket tube responsive to the numerical control signal.

41. A system as defined in claim 40,
wherein the bracket body is formed in a mold;
wherein the electrode includes a traveling wire electrode to cut perimeter portions of the bracket tube to form the bracket tube; and
wherein the electrical discharge device further comprises a die-sinker-electrical discharge electrode to form a starter hole portion of the cutting pattern located at the cutting pattern starting point.

42. A system as defined in claim 40,
wherein the bracket slot has a closed base end, a closed distal end, and two spaced-apart sides extending therebetween spaced apart to define a bracket slot width;
wherein a portion of the electrical discharge cutting pattern includes a first transverse extension extending into the bracket body from one of the spaced-apart sides adjacent the closed base and a second transverse extension extending into the bracket body from the other one of the spaced-apart sides adjacent the closed base to thereby define a bracket slot undercut having an undercut width, the undercut width exceeding the bracket slot width; and
wherein the electrical discharge device control instructions include those to form the bracket slot undercut at the closed base end of the bracket slot.

43. A system as defined in claim 40,
wherein prior to executing the electrical discharge cutting pattern the bracket is connected to a runner which is connected to a mold tree; and
wherein the electrical discharge device control instructions include those to cut the bracket from the mold tree.

* * * * *

UNITED STATES PATENT AND TRADEMARK OFFICE
CERTIFICATE OF CORRECTION

PATENT NO.        : 7,751,925 B2                                              Page 1 of 1
APPLICATION NO.   : 11/583103
DATED             : July 6, 2010
INVENTOR(S)       : Ruedger Rubbert It is certified that error appears in the above-identified patent and that said Letters Patent is hereby corrected as shown below:

Column 20
Line 11; In Claim 1, delete "conununication" and insert -- communication --, therefor.
Line 20; In Claim 1, delete "bracket slot" and insert -- bracket slot, --, therefor.

Column 22
Line 16; In Claim 11, delete "the" and insert -- an --, therefor.
Line 57; In Claim 14, delete "eletrical" and insert -- electrical --, therefor.

Signed and Sealed this

Twelfth Day of October, 2010

David J. Kappos
*Director of the United States Patent and Trademark Office*